(12) United States Patent
Suehiro et al.

(10) Patent No.: US 11,272,907 B2
(45) Date of Patent: Mar. 15, 2022

(54) FECES SAMPLING SHEET

(71) Applicants: Yamaguchi University, Yamaguchi (JP); EIKEN KAGAKU KABUSHIKI KAISHA, Tokyo (JP)

(72) Inventors: Yutaka Suehiro, Yamaguchi (JP); Tomomi Hoshida, Yamaguchi (JP); Takahiro Yamasaki, Yamaguchi (JP)

(73) Assignees: YAMAGUCHI UNIVERSITY, Yamaguchi (JP); EIKEN KAGAKU KABUSHIKI KAISHA, Tokyo (JP)

( * ) Notice: Subject to any disclaimer, the term of this patent is extended or adjusted under 35 U.S.C. 154(b) by 346 days.

(21) Appl. No.: 16/320,312

(22) PCT Filed: Jul. 26, 2017

(86) PCT No.: PCT/JP2017/026993
§ 371 (c)(1),
(2) Date: Jan. 24, 2019

(87) PCT Pub. No.: WO2018/021390
PCT Pub. Date: Feb. 1, 2018

(65) Prior Publication Data
US 2019/0239862 A1    Aug. 8, 2019

(30) Foreign Application Priority Data
Jul. 26, 2016 (JP) .............................. JP2016-146168

(51) Int. Cl.
*A61B 10/00* (2006.01)
*G01N 33/48* (2006.01)
(Continued)

(52) U.S. Cl.
CPC ............ *A61B 10/0038* (2013.01); *E03D 9/00* (2013.01); *G01N 33/48* (2013.01); *A61F 5/451* (2013.01);
(Continued)

(58) Field of Classification Search
CPC ...... A61B 10/0038; G01N 33/48; G01N 1/10; A61F 5/451; A61F 2005/4402
See application file for complete search history.

(56) References Cited

U.S. PATENT DOCUMENTS 3,588,921 A * 6/1971 Nagel ................ A61B 10/0038
4/245.4
2015/0038875 A1 * 2/2015 Poland ............... A61B 10/0038
600/562

FOREIGN PATENT DOCUMENTS

FR    2740672 A1 * 5/1997 ......... A61B 10/0038
JP    7-6760         1/1995
(Continued)

OTHER PUBLICATIONS

Google Patents, "Translation of WO 2004075757 A1", 2004, https://patents.google.com/patent/WO2004075757A1/en?oq=WO+2004075757+A1+ (Year: 2004).*

(Continued)

*Primary Examiner* — Tatyana Zalukaeva
*Assistant Examiner* — Hans Kaliher
(74) *Attorney, Agent, or Firm* — Wenderoth, Lind & Ponack, L.L.P.

(57) ABSTRACT

A feces collection sheet (S), which has a cylindrical shape and includes: an upper sheet (1) having a feces receiving portion (2) in a center of the upper sheet (1); and a lower sheet (9), which is provided so as to extend from both of a right-side edge portion and a left-side edge portion of the upper sheet (1) and is configured to define a gap with the upper sheet (1) to allow insertion of a toilet seat therethrough. The upper sheet (1) and the lower sheet (9) are made of a material having a water-soluble material property. The upper sheet (1) has a folded piece portion (10) adapted to be unfolded to enable the feces receiving portion (2) to (Continued)

form a three-dimensional shape that bulges toward the lower sheet (9).

2 Claims, 16 Drawing Sheets

(51) Int. Cl.
  *E03D 9/00* (2006.01)
  *G01N 1/04* (2006.01)
  *A61F 5/451* (2006.01)
  *A61F 5/44* (2006.01)
(52) U.S. Cl.
  CPC ........ *A61F 2005/4402* (2013.01); *G01N 1/04* (2013.01)

(56) References Cited

FOREIGN PATENT DOCUMENTS

| | | | |
|---|---|---|---|
| JP | 7-270403 | 10/1995 | |
| JP | 10-68726 | 3/1998 | |
| JP | 2004-085520 | 3/2004 | |
| JP | 2005-17252 | 1/2005 | |
| JP | 3200606 | 10/2015 | |
| WO | WO-2004075757 A1 * | 9/2004 | ......... A61B 10/0038 |
| WO | WO-2008020776 A1 * | 2/2008 | ........... B65D 21/086 |
| WO | WO-2013129930 A1 * | 9/2013 | ......... A61B 10/0038 |

OTHER PUBLICATIONS

International Search Report dated Oct. 24, 2017 in International (PCT) Application No. PCT/JP2017/026993.

* cited by examiner

FECES SAMPLING SHEET

TECHNICAL FIELD

The present invention relates to a feces collection sheet, which has a cylindrical shape, including: an upper sheet having a feces receiving portion formed in a center of the upper sheet; and a lower sheet, which is provided so as to extend from both of a right-side edge portion and a left-side edge portion of the upper sheet and is configured to define a gap with the upper sheet to allow insertion of a toilet seat therethrough.

BACKGROUND ART

A fecal examination is carried out all over the world in examinations for digestive system diseases including colorectal cancer, examinations for bacteria infections and parasitic infections, and the like. In particular, in recent years, the number of fecal occult blood tests has been rapidly increasing in screening examinations for colorectal cancer, and at least about seven million fecal occult blood tests are carried out per year in Japan.

Further, in combination with a genome analysis project for human resident flora in the late 2000's, which was carried out mainly in Europe and the United States, a study on "intestinal flora" has been rapidly developed and has indicated an important role in various diseases of the immune system, the metabolic system, the nervous system, and the like. On a worldwide basis, two-hundred eighty-nine million dollars have been funded to researches on gut bacterial flora in about five years after 2008. In addition, the value is increasing year by year, and hence it can be said that the gut bacterial flora research is a field of research that is attracting remarkable attention. Even in the gut bacterial flora research, "feces sample collection" is essentially required. Therefore, it is considered that the fecal examinations in the above-mentioned field of research are increasingly carried out in the future.

As a method of collecting the feces sample for the fecal examination, in a case of a Japanese-style toilet bowl, the following method is carried out. A piece of toilet paper or newspaper, or the like is placed directly on the toilet bowl or is placed in the toilet bowl. After defecation thereon, feces are picked through use of a feces collection stick by allowing the feces to adhere thereto, or are scooped up through use of a feces collection cup. Meanwhile, western-style toilet bowls are increasing in recent years. In a case of the western-style toilet bowl described above, the following method is generally carried out. After apiece of toilet paper or the like is placed on the near side of a water storage portion of the toilet bowl, a sample provider sits so as to face in a direction opposite to a direction in which the sample provider faces in general use, and defecates on the piece of toilet paper or the like to collect the feces sample. However, there are following problems. Specifically, the sample provider is required to be careful so as not to get the piece of toilet paper wet. Moreover, the feces are required to be prevented from dropping into the water storage portion in the toilet bowl. Further, the defecation is not smooth because a sitting position is different from a normal sitting position.

In the case of the western-style toilet bowl, there has been carried out a method that allows defecation on a water-soluble defecation sheet placed on a water surface of water in the water storage portion of the toilet bowl. As the water-soluble defecation sheet to be used for the method described above, there have been proposed a feces collection sheet (see Patent Literature 1) and a feces receiving sheet for feces collection (see Patent Literature 2). The feces collection sheet has one or both of surfaces of a base material made of water-dispersible paper, which are subjected to a water-resistance treatment with a water resisting agent to control water dispersibility in terms of time. The feces receiving sheet for feces collection has at least one surface of a sheet main body made of water-soluble paper, which is subjected to a water-resistance treatment with a water resisting agent, to control water solubility. However, there arise the following problems. Specifically, feces are required to be collected within a given period of time after the sheet is placed on the water surface. Therefore, smooth defecation is hindered under a psychological pressure that "the sheet may dissolve before the defecation". In a case of urination after the defecation, a blood component adhering on a surface of feces is taken away together with urine because of the absence of a urine exhaust passage. Therefore, a fecal occult blood test cannot be conducted correctly. In a case of urination before or after the defecation, decomposition of the water-soluble sheet is disadvantageously accelerated. As a result, the feces may drop into the water.

Meanwhile, in the case of the western-style toilet bowl, there has been carried out a method of fixing a feces collecting portion to a predetermined position above the water storage portion. As a water-soluble defecation sheet to be used for the above-mentioned method, there have been proposed a collection device for fecal examination (see Patent Literature 3) and a feces collection sheet (see Patent Literature 4) described below. Specifically, with regard to the collection device for fecal examination having been proposed, the collection device for fecal examination includes a collection tape having a length within a range of from 45 cm to 50 cm and a width within a range of from 2.5 cm to 5 cm, double-sided tapes with release paper, and a water-soluble collection mat. The double-sided tapes are applied to a back surface of the collection device so as to be located on both sides of the back surface. The water-soluble collection mat has a release mechanism in the center of an upper surface of the collection tape. The collection device for fecal examination is bonded with releasable tapes on a back side through two holes formed in the collection tape so as to have an appropriate degree of deflection toward the inner side of a toilet bowl. With regard to the feces collection sheet having been proposed, the feces collection sheet includes a water-soluble sheet main body and a water-soluble double-sided adhesive tape. The water-soluble sheet main body has a length L that allows at least both end edge portions to be superposed on right and left edges of a toilet bowl. A feces receiving portion provided in an intermediate portion is formed to have a width that is at least sufficient to receive feces. The double-sided adhesive tape is covered with a release tape. The double-sided adhesive tape is bonded onto one surface of the sheet main body so as to be located at both end edges. However, there arise the following problems. The sheet is required to be fixed with an adhesive such as the tape, and hence work of applying the tape onto an unsanitary toilet bowl or removing the tape therefrom is required. Thus, a hand may touch the unsanitary toilet bowl, and there is hesitation from a hygienical point of view. Further, when the adhesive remains in the toilet bowl, dirt may be liable to adhere to the toilet bowl through subsequent uses of the toilet bowl. In addition, the adhesive has non-water-soluble release paper in many cases. The release paper cannot be flushed in the toilet after being released from the adhesive.

CITATION LIST

Patent Literature

[PTL 1] JP 2005-017252 A
[PTL 2] JP 10-068726 A
[PTL 3] JP 2004-085520 A
[PTL 4] JP 07-270403 A

SUMMARY OF INVENTION

Technical Problem

The present invention has an object to provide a feces collection sheet, which reliably enables collection of feces without being dipped in a water storage portion of a western-style toilet bowl and is mountable to the toilet bowl without use of an adhesive.

Solution to Problem

The inventors of the present invention recognized the need for improvement of a feces collection sheet because of difficulty in appropriate collection of a feces sample with existing feces collection sheets and a problem such as hesitation in terms of hygiene. Therefore, through various improvements, the inventors of the present invention have found that a sheet can be mounted to a toilet seat by forming the sheet into a cylindrical shape even without use of an adhesive. Further, the inventors of the present invention have also found that a feces receiving portion included in the feces collection sheet has mountain creases and valley creases to form a three-dimensional shape that bulges toward a lower sheet so as to allow more efficient feces collection. In this manner, the prevent invention has been achieved.

Specifically, the present invention has the following configurations.

According to a first aspect of the invention, there is provided a feces collection sheet, which has a cylindrical shape, including: an upper sheet having a feces receiving portion in a center of the upper sheet; and a lower sheet, which is provided so as to extend from both of a right-side edge portion and a left-side edge portion of the upper sheet and is configured to define a gap with the upper sheet to allow insertion of a toilet seat therethrough, wherein the upper sheet and the lower sheet are made of a material having a water-soluble material property, and wherein the upper sheet has a folded piece portion to be unfolded to enable the feces receiving portion to form a three-dimensional shape that bulges toward the lower sheet.

According to the first aspect of the invention, the feces collection sheet can be easily and reliably mounted to the toilet seat by simple means of inserting the toilet seat into the gap defined between the upper sheet and the lower sheet.

Further, the feces receiving portion is enabled to form the three-dimensional shape that bulges toward the lower sheet by pushing the folded piece portion of the upper sheet toward the lower sheet to unfold the folded piece portion. Therefore, feces received in the feces receiving portion can be prevented from dropping from the feces receiving portion.

Further, the upper sheet and the lower sheet are made of a material having a water-soluble material property. Therefore, after feces collection, the feces collection sheet can be directly flushed into a flush toilet.

In a second aspect of the invention, the upper sheet and the lower sheet as described in the first aspect of the invention, which are made of the material having the water-soluble material property, are made of water-soluble paper.

According to the second aspect of the invention, the upper sheet and the lower sheet are made of the water-soluble paper. Therefore, the feces collection sheet can be provided at low cost.

In a third aspect of the invention, the folded piece portion of the upper sheet as described in the first or second aspects of the invention has a mountain crease and a valley crease on the feces receiving portion of the upper sheet, end portions of the mountain crease and end portions of the valley crease are fixed, and the feces receiving portion is enabled to form the three-dimensional shape that bulges toward the lower sheet by unfolding a folded piece folded on the mountain crease and the valley crease toward the lower sheet.

According to the third aspect of the invention, the folded piece portion of the upper sheet is pushed toward the lower sheet. As a result, the folded piece folded on the mountain creases and the valley creases is unfolded. In this manner, the feces receiving portion is enabled to form the three-dimensional shape that bulges toward the lower sheet.

In a fourth aspect of the invention, the mountain crease and the valley crease formed on the feces receiving portion of the upper sheet as described in the third aspect of the invention are parallel to each other.

According to the fourth aspect of the invention, the mountain creases and the valley creases formed on the feces receiving portion of the upper sheet are parallel to each other. Therefore, a force of pushing the folded piece portion toward the lower sheet is evenly distributed and transmitted to the mountain creases and the valley creases. Therefore, the folded piece folded on the mountain creases and the valley creases can be smoothly unfolded.

In a fifth aspect of the invention, the mountain crease and the valley crease formed on the feces receiving portion of the upper sheet as described in the fourth aspect of the invention are provided in parallel to a front-and-rear direction of the feces receiving portion.

According to the fifth aspect of the invention, the mountain creases and the valley creases formed on the feces receiving portion of the upper sheet are provided in parallel to the front-and-rear direction of the feces receiving portion. Therefore, the feces receiving portion is enabled to form a stable three-dimensional shape.

In a sixth aspect of the invention, the mountain crease and the valley crease formed on the feces receiving portion of the upper sheet as described in the fourth aspect of the invention are provided in parallel to a right-and-left direction of the feces receiving portion.

According to the sixth aspect of the invention, the mountain creases and the valley creases formed on the feces receiving portion of the upper sheet are provided in parallel to the right-and-left direction of the feces receiving portion. Therefore, the feces receiving portion is enabled to form a stable three-dimensional shape.

In a seventh aspect of the invention, the folded piece portion of the upper sheet as described in the first or second aspects of the invention is formed by folding back a front-side edge portion and a rear-side edge portion of the upper sheet to the back surface side and fixing a right end edge and a left end edge of each of back-side sheet piece portions, which are formed by being folded back, and a right end edge and a left end edge of a top-side sheet piece portion, and the feces receiving portion is enabled to form the three-dimensional shape that bulges toward the lower sheet by bringing the back-side sheet piece portions to the top side of the top-side sheet piece portion so as to open the back-side sheet piece portions outward.

According to the seventh aspect of the invention, the back-side sheet piece portions are brought to the top side of the top-side sheet piece portion so as to be opened outward. In this manner, the feces receiving portion is enabled to form the three-dimensional shape that bulges toward the lower sheet. Therefore, the feces received in the feces receiving portion can be prevented from dropping from the feces receiving portion.

In an eighth aspect of the invention, the upper sheet and the lower sheet as described in the seventh aspect of the invention are formed of two sheet base material pieces obtained by folding a sheet base material having a rectangular shape in half, one of the sheet base material pieces is used as the top-side sheet piece portion of the upper sheet, whereas two cutting lines being parallel to a right-and-left direction of the feces collection sheet are formed in another of the sheet base material pieces, portions located on outer sides of the two cutting lines are used as the back-side sheet piece portions that form the folded piece portion of the upper sheet, whereas a portion located on an inner side of the two cutting lines is used as the lower sheet, and, after the two sheet base material pieces obtained by folding the sheet base material in half are superposed on one another, three open end edges of the two sheet base material pieces having been superposed on one another are fixed to each other.

According to the eighth aspect of the invention, the structure is simple. Therefore, the feces collection sheet is easy to manufacture and can be provided at low cost.

Advantageous Effects of Invention

With the feces collection sheet according to one embodiment of the present invention, the feces receiving portion is enabled to form the three-dimensional shape that bulges toward the lower sheet. Therefore, the feces received in the feces receiving portion can be prevented from dropping from the feces receiving portion. Further, the feces collection sheet does not come into contact with the water storage portion of the toilet bowl. Therefore, there is no fear that the feces collection sheet may come into contact with water to dissolve during defecation, thereby enabling the defecation at desired pace. Further, the feces collection sheet can be mounted to the toilet seat by simple means of inserting the toilet seat through the gap defined between the upper sheet and the lower sheet without use of an adhesive for mounting the feces collection sheet to the toilet seat. Therefore, the mounting and removing are enabled in a hygienically ensured manner. At the same time, dirt can be prevented from adhering to the toilet bowl. Further, the feces collection sheet is made of the water-soluble material. Therefore, the entire sheet can be directly flushed into the flush toilet after the feces collection.

DESCRIPTION OF EMBODIMENT

Figure 1:
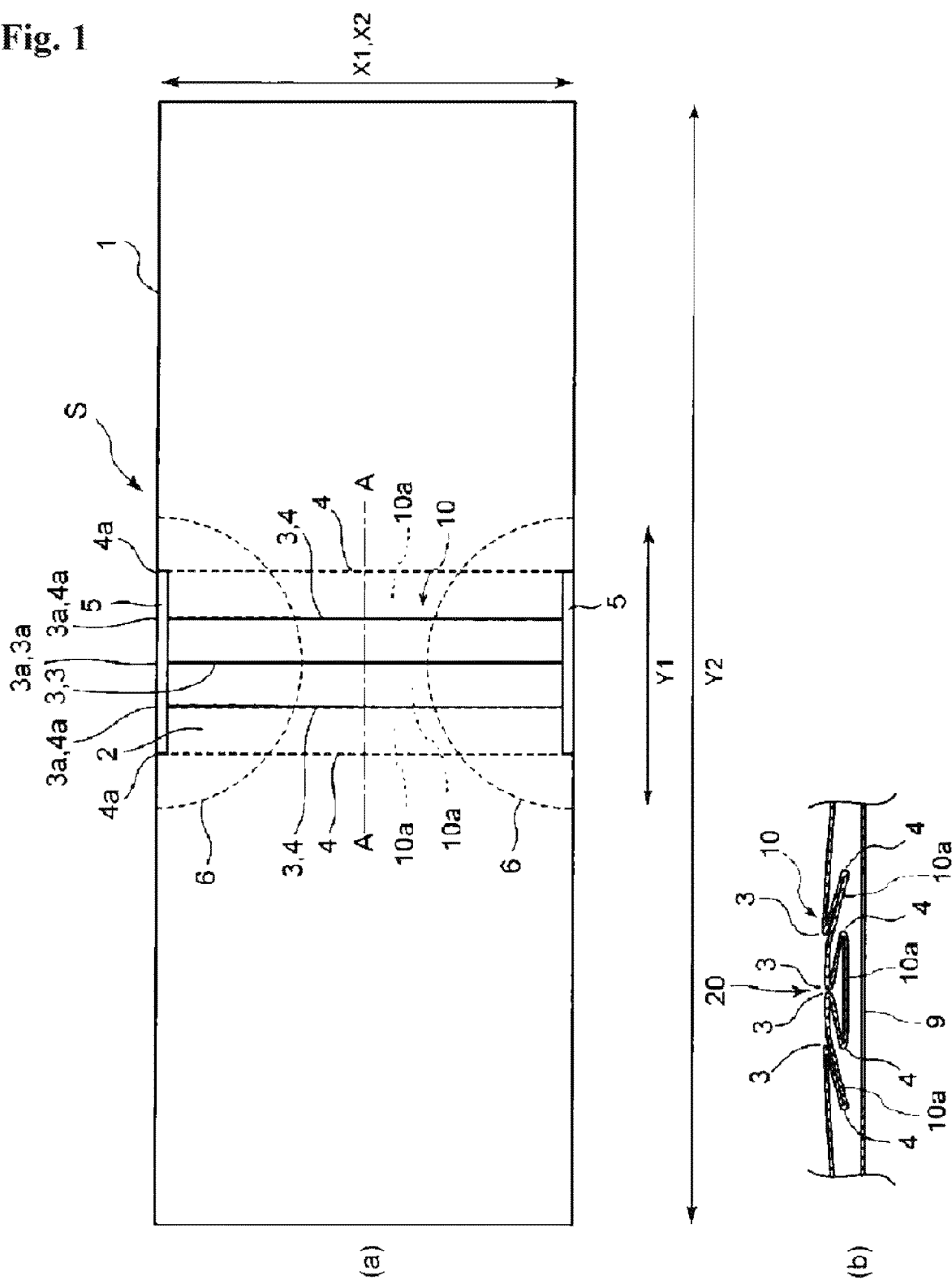
FIG. 1(a) is a plan view for illustrating a first example of an embodiment of a feces collection sheet according to the present invention.
FIG. 1(b) is a sectional view of a feces receiving portion illustrated in FIG. 1(a), which is taken along the line A-A in a right-and-left direction.

A feces collection sheet according to the present invention, which has a cylindrical shape, includes: an upper sheet having a feces receiving portion in a center of the upper sheet; and a lower sheet, which is provided so as to extend from both of a right-side edge portion and a left-side edge portion of the upper sheet and is configured to define a gap with the upper sheet to allow insertion of a toilet seat therethrough. The upper sheet and the lower sheet are made of a material having a water-soluble material property. The upper sheet has a folded piece portion to be unfolded to enable the feces receiving portion to form a three-dimensional shape that bulges toward the lower sheet.

The upper sheet has a length in a right-and-left direction, which falls within a range of from 45 cm to 70 cm. Through setting of the length of the upper sheet to fall within the range of from 45 cm to 70 cm, the toilet seat is inserted into the gap defined between the upper sheet and the lower sheet.

In this manner, the feces receiving portion of the upper sheet can be positioned at a predetermined position above a water storage portion inside a toilet bowl without allowing the feces collection sheet to come into contact with the water storage portion and without use of an adhesive such as a seal.

A width between a front-side edge portion and a rear-side edge portion of the feces receiving portion of the upper sheet falls within a range of from 8 cm to 30 cm, preferably, within a range of from 10 cm to 25 cm, more preferably, within a range of from 12 cm to 19 cm in a state in which the folded piece portion is unfolded. When the width between the front-side edge portion and the rear-side edge portion of the feces receiving portion is smaller than 8 cm, it is difficult to receive feces. Therefore, there is a high risk that part or all of the feces may not remain on the feces collection sheet. When the width is larger than 30 cm, there is a high risk that the upper sheet may dissolve to drop the received feces from the feces collection sheet in case of urination.

Although a length of the feces receiving portion in the right-and-left direction (longitudinal direction) is not particularly limited, there are exemplified a range of from 5 cm to 35 cm, preferably, within a range of from 10 cm to 25 cm, more preferably, within a range of from 12 cm to 19 cm in the state in which the folded piece portion is unfolded.

The feces receiving portion, which is formed in the center of the upper sheet and is configured to receive feces, has the folded piece portion. The folded piece portion is enabled to form a three-dimensional shape that bulges toward the lower sheet. With the configuration described above, the feces can be placed inside the three-dimensional shape. The feces received in the feces receiving portion of the upper sheet is more easily held on a surface of the lower sheet. In addition, feces can be prevented from adhering to buttocks at the time of defecation. Before the use, the folded piece portion can be brought into a flat form without a three-dimensional shape by folding the folded piece portion. Thus, the entire feces collection sheet can be folded into a compact flat shape. In this manner, before a sample provider goes to a toilet, the feces collection sheet can be stored in a pocket or the like. At the same time, when the feces collection sheet is to be distributed together with a feces collection kit including a stick for feces collection and a feces collection cup, the feces collection sheet can be accommodated in a slight space in a container for the feces collection kit.

Further, the folded piece portion is unfolded to form the three-dimensional shape that bulges toward the lower sheet. As a result, a risk of causing uncleanliness on buttocks with excreted feces can be reduced. Further, a sufficient amount of feces is required for a sample for a fecal DNA test or an intestinal flora test for colorectal cancer screening. Collection of a sufficient amount of feces is further facilitated with the formation of the three-dimensional shape.

Further, breakdown of the feces receiving portion in water is reduced by forming the sheet to have a plurality of layers such as two layers, three layers, or four layers, increasing a thickness of the feces receiving portion to be larger than that of a portion other than the feces receiving portion, or increasing a water resistance thereof to be larger than that of the portion other than the feces receiving portion. In this manner, even if the feces receiving portion gets wet with urine or water in a shower toilet, the feces receiving portion can be less liable to breakdown. In addition, through increase of a weight of the feces receiving portion with respect to that of the entire upper sheet, the entire feces receiving portion can be more naturally deflectable toward the lower sheet.

A width of the portion of the upper sheet other than the feces receiving portion in a front-and-rear direction (transverse direction) is not particularly limited as long as the feces receiving portion can be suspended at a predetermined position of a western-style flush toilet bowl so as not to come into contact with a water storage portion, and may fall within a range of from 1 cm to 40 cm, a range of from 2 cm to 35 cm, a range of from 5 cm to 30 cm, a range of from 8 cm to 25 cm, a range of from 10 cm to 20 cm, or a range of from 12 cm to 19 cm. In view of reduction of the amount of feces collection sheet to be flushed so as to reduce a burden at the time of flushing, the width in the front-and-rear direction is only required to be reduced. In view of prevention of tear due to breakdown of the upper sheet with sweat or a physical force when the sample provider sits on the upper sheet, the width in the front-and-rear direction is only required to be increased. The width of the feces receiving portion and the width of the portion of the upper sheet other than the feces receiving portion in the front-and-rear direction may be the same or different. When the widths are the same, processing for the feces collection sheet is facilitated.

The portion of the upper sheet other than the feces receiving portion may be formed by arranging in parallel a plurality of sheets such as two, three, four, five, six, or seven sheets each having a smaller width in the front-and-rear direction than that of the feces receiving portion as long as the feces receiving portion can be suspended at the predetermined portion at which the feces receiving portion does not come into contact with the water storage portion of the western-type flush toilet bowl. In view of facility of mounting the feces collection sheet to the toilet seat, however, it is preferred that the portion of the upper sheet other than the feces receiving portion be formed of a smaller number of sheets, more preferably, one sheet.

The portion of the upper sheet other than the feces receiving portion is placed on the toilet seat before a defecating person sits on the toilet seat. Therefore, even on the toilet to be used by an unspecified number of persons, for example, in a hospital, a sense of ease can be provided in terms of hygiene. In addition, even when a temperature of the toilet seat is low during cold time such as a winter season, an area of thighs of the defecating person, which is in direct contact with the toilet seat, is reduced. Thus, coldness felt when the defecating person sits on the toilet seat can be reduced.

The lower sheet is provided so as to extend from both of a right-side edge portion and a left-side edge portion of the upper sheet and is configured to define a gap with the upper sheet to allow insertion of the toilet seat therethrough. The upper sheet and the lower sheet are configured to form a cylindrical shape. With the configuration described above, the feces collection sheet can hold the feces in the feces receiving portion for a long period of time without fear of breakdown with water. Therefore, when a sample for a fecal occult blood test is collected, work of evenly scraping a surface of feces can be easily carried out. Further, a sufficient amount of feces can be easily collected for a fecal DNA test or an intestinal flora test for colorectal cancer screening.

Although a width of the lower sheet in the front-and-rear direction (transverse direction) is not particularly limited, the width may fall within a range of from 1 cm to 40 cm, a range of from 2 cm to 35 cm, a range of from 5 cm to 30 cm, a range of from 8 cm to 25 cm, a range of from 10 cm to 20 cm, or a range of from 12 cm to 19 cm. In view of reduction of the amount of feces collection sheet to be flushed so as to reduce the burden at the time of flushing, the width in the front-and-rear direction is only required to be reduced.

Although the width of the feces receiving portion and the width of the lower sheet in the front-and-rear direction (transverse direction) may be the same or different, processing for the feces collection sheet is facilitated when the widths are the same. The lower sheet may be formed by arranging in parallel a plurality of sheets such as two, three, four, five, six, or seven sheets each having a smaller width in the front-and-rear direction than that of the feces receiving portion. In view of facility of mounting the feces collection sheet to the toilet seat, however, it is preferred that lower sheet be formed of a smaller number of sheets, more preferably, one sheet.

A length of the lower sheet in the right-and-left direction (longitudinal direction) falls within a range of from 45 cm to 70 cm. Although the length of the upper sheet and the length of the lower sheet in the right-and-left direction may be the same or different, the processing for the feces collection sheet is facilitated when the lengths are the same.

A material of the upper sheet and the lower sheet is not particularly limited as long as the material has a water-soluble material property. As the water-soluble material property in the present invention, there is exemplified a material property that allows breakdown in 90 seconds or less, preferably, 60 seconds or less, more preferably, 30 seconds or less, further preferably, a range of from 5 seconds to 30 seconds, in a breakdown test defined in Japanese Industrial Standards (JIS) P4501. As a material having the material property described above, there are exemplified water-soluble paper, a water-soluble polymer such as water-soluble polyvinyl alcohol, and water-soluble non-woven fabric. Because of the water-soluble material property, after the completion of the collection of feces, an upper sheet 1 and a lower sheet 9 are partially torn to allow removal from the toilet seat so that an entire feces collection sheet S can be directly flushed away.

Further, the upper sheet and/or the lower sheet may be embossed. When the upper sheet and/or the lower sheet are/is embossed, the thighs of the defecating person can be prevented from adhering to the upper sheet so as not to easily tear the upper sheet at the time of defecation, or comfort of the defecating person in use of the feces collection sheet can be improved.

Although a method of manufacturing the feces collection sheet is not particularly limited, the feces collection sheet may be manufactured with one sheet or a plurality of sheets. In a fixing step in the manufacture, there are exemplified a method using a water-soluble tape, a method using a water-soluble adhesive, a fixing method with a stapleless stapler, and a fixing method with heat or an ultrasonic wave.

EXAMPLES

Examples of the feces collection sheet according to the present invention are now described in detail with reference to the drawings.

First Example

Figure 2:
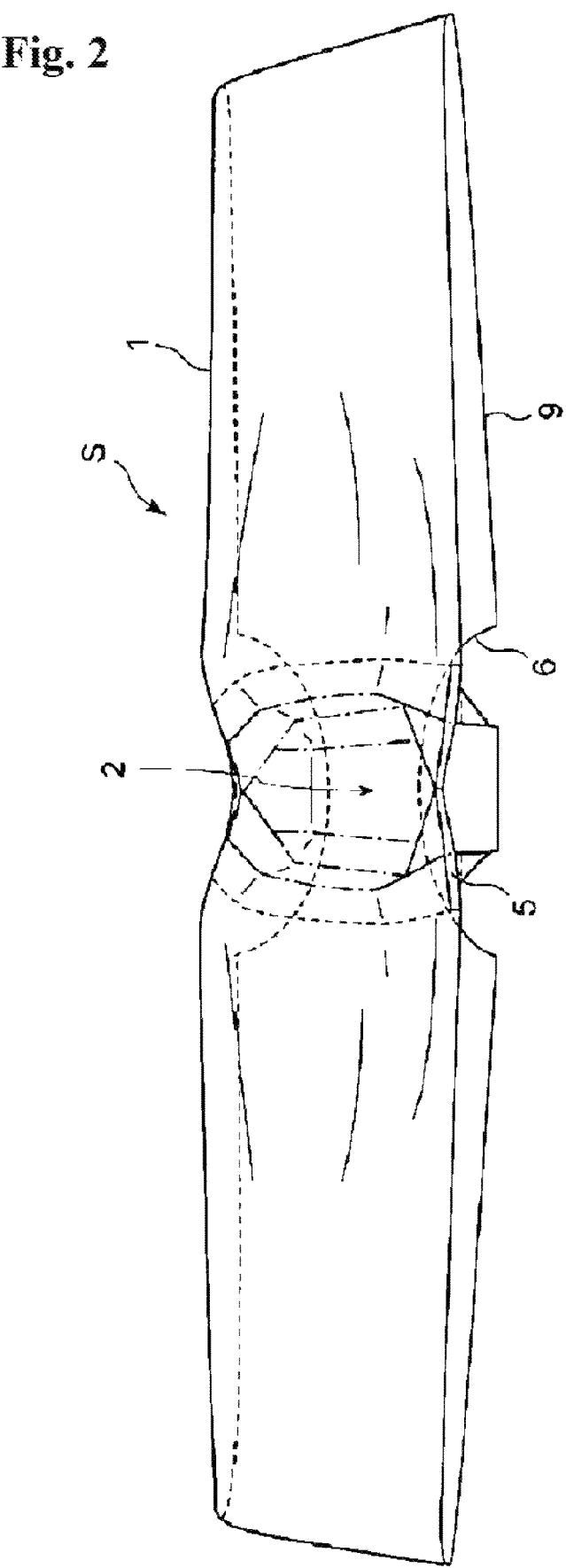
FIG. 2 is a perspective view for illustrating a state in which the feces receiving portion of the feces collection sheet illustrated in FIG. 1 is unfolded to bulge toward a lower sheet to form a three-dimensional shape.
Figure 3:
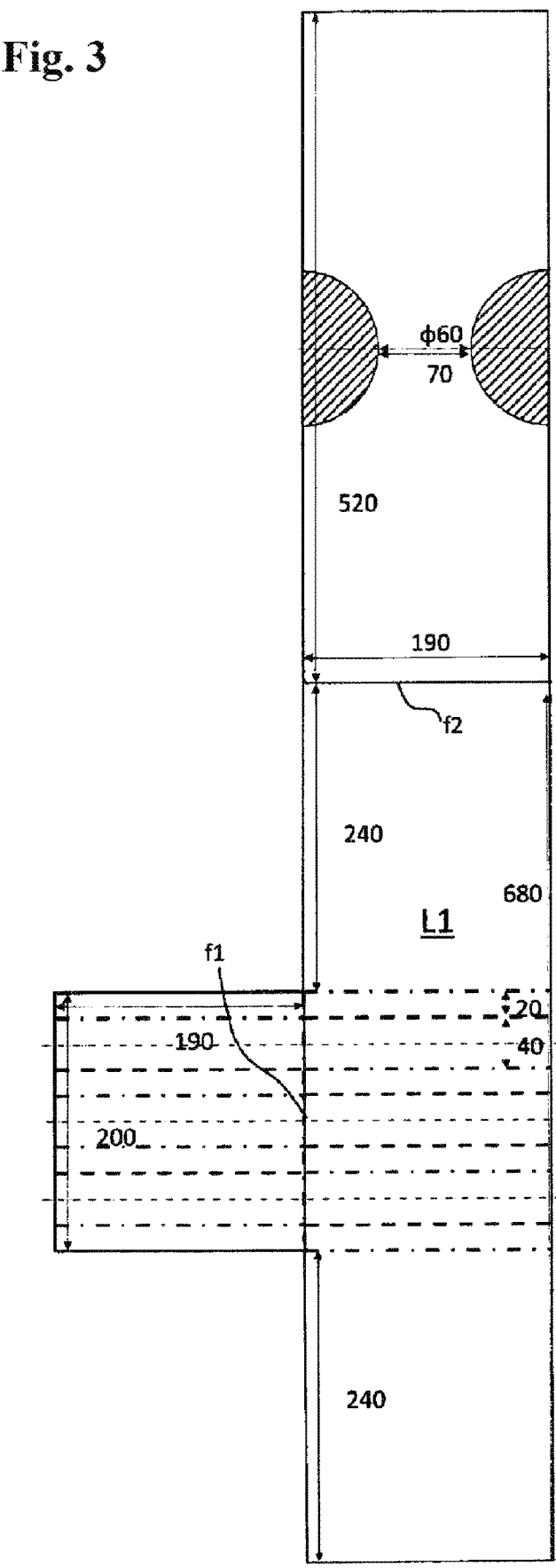
FIG. 3 is a plan view for illustrating a sheet made of paper to be used for manufacture of the feces collection sheet of the first example illustrated in FIG. 1.
Figure 4:
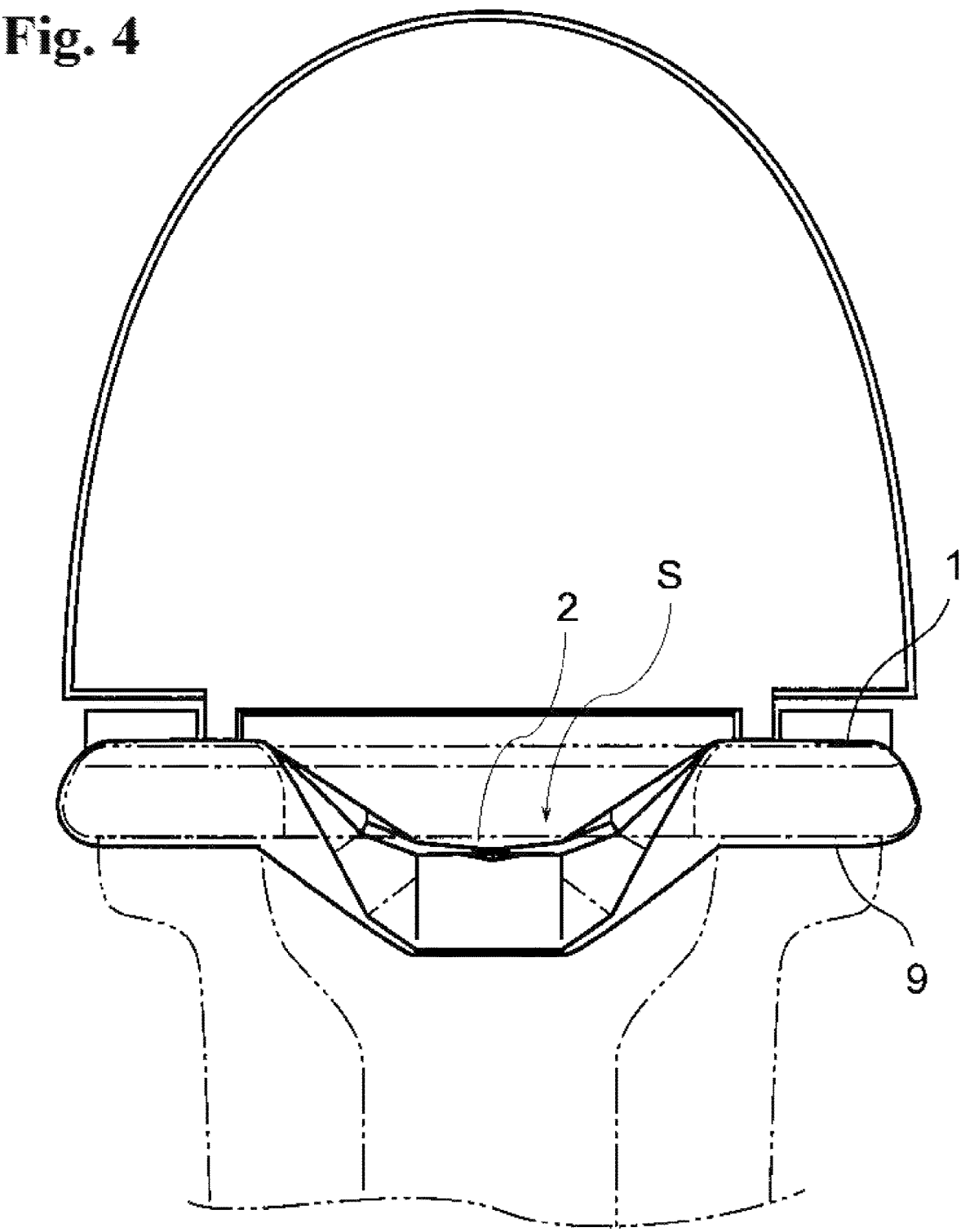
FIG. 4 is a front view for illustrating a state in which the feces collection sheet of the first example illustrated in FIG. 1 is placed on a toilet seat.
Figure 5:
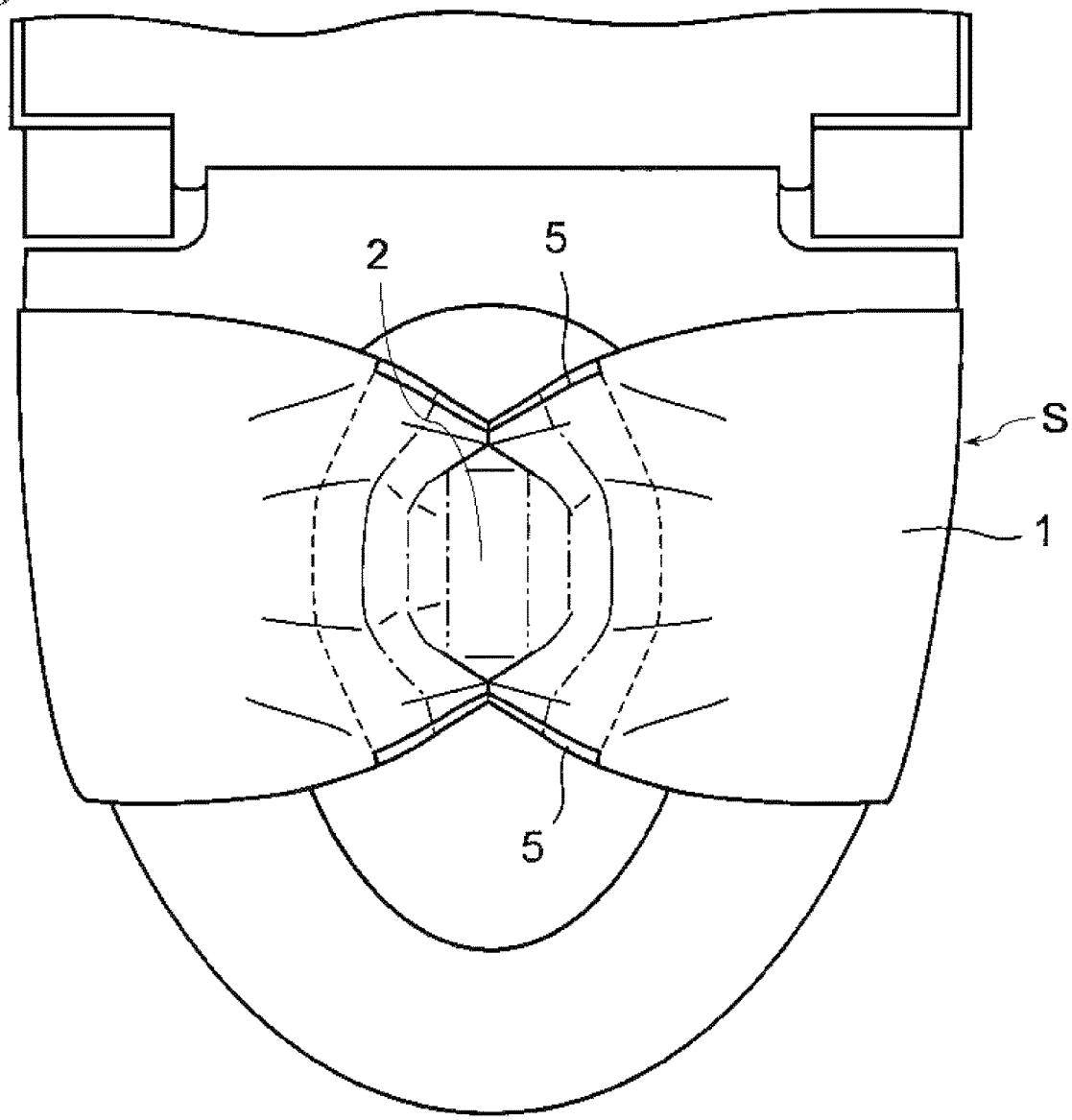
FIG. 5 is a plan view for illustrating the state in which the feces collection sheet of the first example illustrated in FIG. 1 is placed on the toilet seat.

FIG. 1(*a*) is a plan view for illustrating a first example of a feces collection sheet according to the present invention. FIG. 1(*b*) is a sectional view of a feces receiving portion illustrated in FIG. 1(*a*), which is taken along the line A-A in a right-and-left direction. FIG. 2 is a perspective view for illustrating a state in which the feces receiving portion of the feces collection sheet illustrated in FIG. 1 is unfolded to bulge toward a lower sheet to form a three-dimensional shape. FIG. 3 is a plan view for illustrating a sheet made of paper to be used for manufacture of the feces collection sheet of the first example illustrated in FIG. 1. FIG. 4 is a front view for illustrating a state in which the feces collection sheet of the first example illustrated in FIG. 1 is placed on a toilet seat. FIG. 5 is a plan view for illustrating the state in which the feces collection sheet of the first example illustrated in FIG. 1 is placed on the toilet seat.

A feces collection sheet S of the first example includes an upper sheet 1 and a lower sheet 9. The upper sheet 1 has a feces receiving portion 2 formed in a center of the upper sheet 1. The lower sheet 9 is provided so as to extend from both of a right-side edge portion and a left-side edge portion of the upper sheet 1. As a material of the upper sheet 1 and the lower sheet 9, a material having a water-soluble material property is used. The upper sheet 1 and the lower sheet 9 form a cylindrical shape having a gap for allowing insertion of the toilet seat therethrough. The upper sheet 1 has a folded piece portion 10 to be unfolded to enable the feces receiving portion 2 to form the three-dimensional shape that bulges toward the lower sheet 9.

In the first example, as illustrated in FIG. 1(*a*) and FIG. 1(*b*), the folded piece portion 10 is folded into the feces receiving portion 2 on mountain creases 3 and valley creases 4 which are provided in parallel to the front-and-rear direction of the feces receiving portion 2. One or both of end portions 3*a* of each of the mountain creases 3 and/or end portions 4*a* of each of the valley creases 4 are entirely or partially fixed so as not to be unfoldable.

When one or both sides of the end portions 3*a* of each of the mountain creases 3 and the end portions 4*a* of each of the valley creases 4 are entirely or partially fixed, the feces receiving portion 2 is enabled to form the three-dimensional shape that bulges toward the lower sheet 9 to allow easier collection of the feces by unfolding a folded piece 10*a* of the folded piece portion 10 folded on the mountain creases 3 and the valley creases 4. Further, through application of a tension to a front-side edge portion and/or a rear-side edge portion, the feces received in the vicinity of the end portions 3*a* of the mountain creases 3 and/or the end portions 4*a* of the valley creases 4 can be prevented from dropping from the feces receiving portion 2.

Although a method of fixing the end portions 3*a* of the mountain creases 3 and/or the end portions 4*a* of the valley creases 4 is not particularly limited, there are exemplified a method using a water-soluble adhesive, a method of fixing the end portions 3*a* of the mountain creases 3 and/or the end portions 4*a* of the valley creases 4 with a water-soluble seal by applying the water-soluble seal thereon, a fixing method with a stapleless stapler, and a fixing method with heat or an ultrasonic wave. In the first example, the end portions 3*a* of the mountain creases 3 and the end portions 4*a* of the valley creases 4 are fixed with water-soluble tapes 5 each having a length of 8 cm.

In the first example, a width X1 between the front-side edge portion and the rear-side edge portion in a state in which the feces receiving portion 2 is folded is 19 cm, and a width Y1 in the right-and-left direction is 12 cm. A width X2 of a portion of the upper sheet 1 other than the feces receiving portion 2 is also 19 cm. A length Y2 of the upper sheet 1 in the right-and-left direction is 52 cm.

The lower sheet 9 having the same length and width as those of the upper sheet 1 is provided so as to extend from both of the right-side edge portion and the left-side edge portion of the upper sheet 1 to form the cylindrical shape, which is not visible under the upper sheet 1, and hence is not illustrated in FIG. 1(*a*). Cutting portions 6 each indicated by the broken line are formed in both of the front-side edge portion and the rear-side edge portion of the lower sheet 9, respectively.

For the mountain creases 3 and the valley creases 4 formed on the feces receiving portion 2 including the folded piece portion 10, as illustrated in FIG. 1(b), the mountain creases 3 are positioned on the front side and the valley creases 4 are positioned on the rear side with respect to a center 20 of the feces receiving portion 2.

The folded piece portion 10 configured as described above is pushed toward the lower sheet 9 to be unfolded from the center 20 of the feces receiving portion 2 in the right-and-left direction. As a result, as illustrated in FIG. 2, the feces receiving portion 2 forms the three-dimensional shape that bulges toward the lower sheet 9.

The width X1 between the front-side edge portion and the rear-side edge portion of the feces receiving portion 2 formed into the three-dimensional shape falls within a range of from 8 cm to 19 cm, and the length Y1 in the right-and-left direction falls within a range of from 12 cm to 16 cm. The width X1 is further reduced when a force is applied in the front-and-rear direction.

The material of the upper sheet 1 and the lower sheet 9 is not particularly limited as long as the material has a water-soluble material property. In the first example, water-soluble paper is used as the material of the upper sheet 1 and the lower sheet 9.

Quality performance of the water-soluble paper used in the first example is as follows.
(1) Thickness of paper 0.06 mm/sheet
(2) Basis weight 25 g/m$^2$
(3) Tensile strength (gf/25 mm)
   MD 2,750 g
   CD 750 g
(4) Ease of breakdown (second) 30 seconds or less Next, an example of a method of manufacturing the feces collection sheet S of the first example is described with reference to FIG. 3.

First, after a sheet L1 made of paper is prepared as illustrated in FIG. 3, the feces collection sheet S is manufactured in the following steps. Numerical values in FIG. 3 represent lengths (mm).
(1) Hatched portions of the sheet L1 are cut and removed. The sheet L1 is perforated along a line f2.
(2) The sheet L1 is folded on a line f1 to form the feces receiving portion in two layers. One end of the feces receiving portions is fixed at two positions with a stapleless stapler.
(3) Four mountain creases (indicated by the alternate long and short dash lines) and four valley creases (indicated by the chain lines) are formed.
(4) The mountain creases are brought to folded edges toward the center so as to pleat the sheet L1.
(5) Both ends of the mountain creases and both ends of the valley creases are fixed with the water-soluble tapes.
(6) The sheet L1 is folded on the line f2, and the end portions are fixed with the stapleless stapler.

In order to mount the feces collection sheet S of the first example, which is configured as described above, to the toilet seat, the toilet seat is brought upright in a vertical direction or the toilet seat is lifted up from the toilet bowl by hand. After that, the toilet seat is inserted into the gap defined between the upper sheet 1 and the lower sheet 9 included in the feces collection sheet S. Then, after the feces collection sheet S is placed on the far side, the toilet seat is placed on the toilet bowl.

Next, a position of the feces receiving portion 2 is adjusted so that the feces are easily received. Then, the entire upper sheet 1 is gently pushed toward the lower layer to unfold the folded piece portion 10 so that the feces receiving portion 2 is unfolded to form the three-dimensional shape that bulges toward the lower sheet 9 (see FIG. 4 and FIG. 5).

The end portions 3a of the mountain creases 3 and the end portions 4a of the valley creases 4 of the unfolded folded piece portion 10 are fixed with the water-soluble tapes 5. Therefore, when the feces receiving portion 2 is unfolded, the water-soluble tapes 5 are curved inward by about 1 cm to 5.5 cm. As a result, the breakdown of the upper sheet 1 due to wetting of the upper sheet 1 with urine can be further prevented, and the risk that urine may be mixed with a feces sample can be reduced. A tension is generated in both of the front-side edge portion and the rear-side edge portion due to the water-soluble tapes 5. Therefore, the feces can be further prevented from dropping from both of the front-side edge portion and the rear-side edge portion of the feces receiving portion 2.

Second Example

Figure 6:
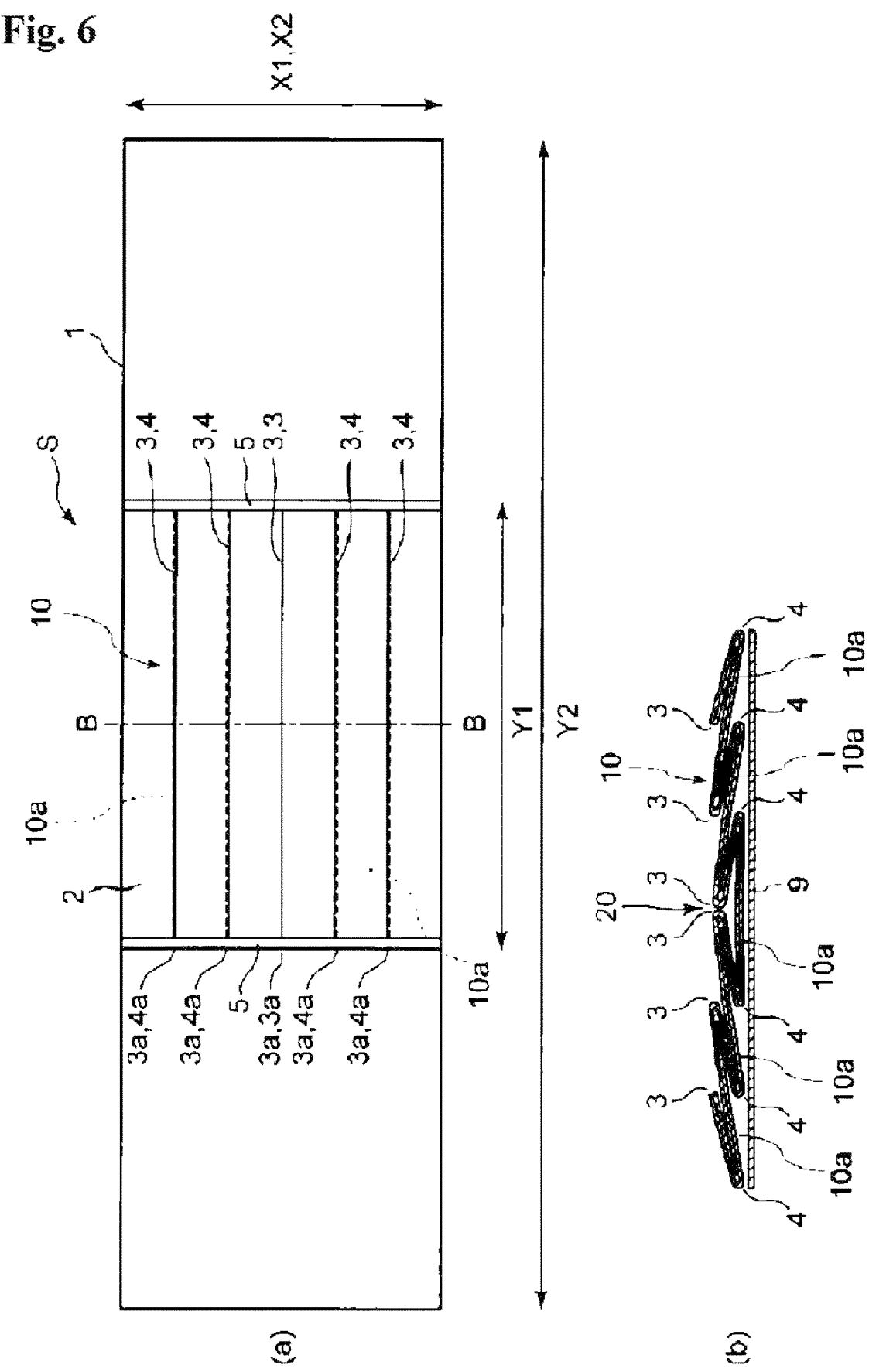
FIG. 6(a) is a plan view for illustrating a second example of the embodiment of the feces collection sheet according to the present invention.
FIG. 6(b) is a sectional view of a feces receiving portion illustrated in FIG. 6(a), which is taken along the line B-B in a front-and-rear direction.
Figure 7:
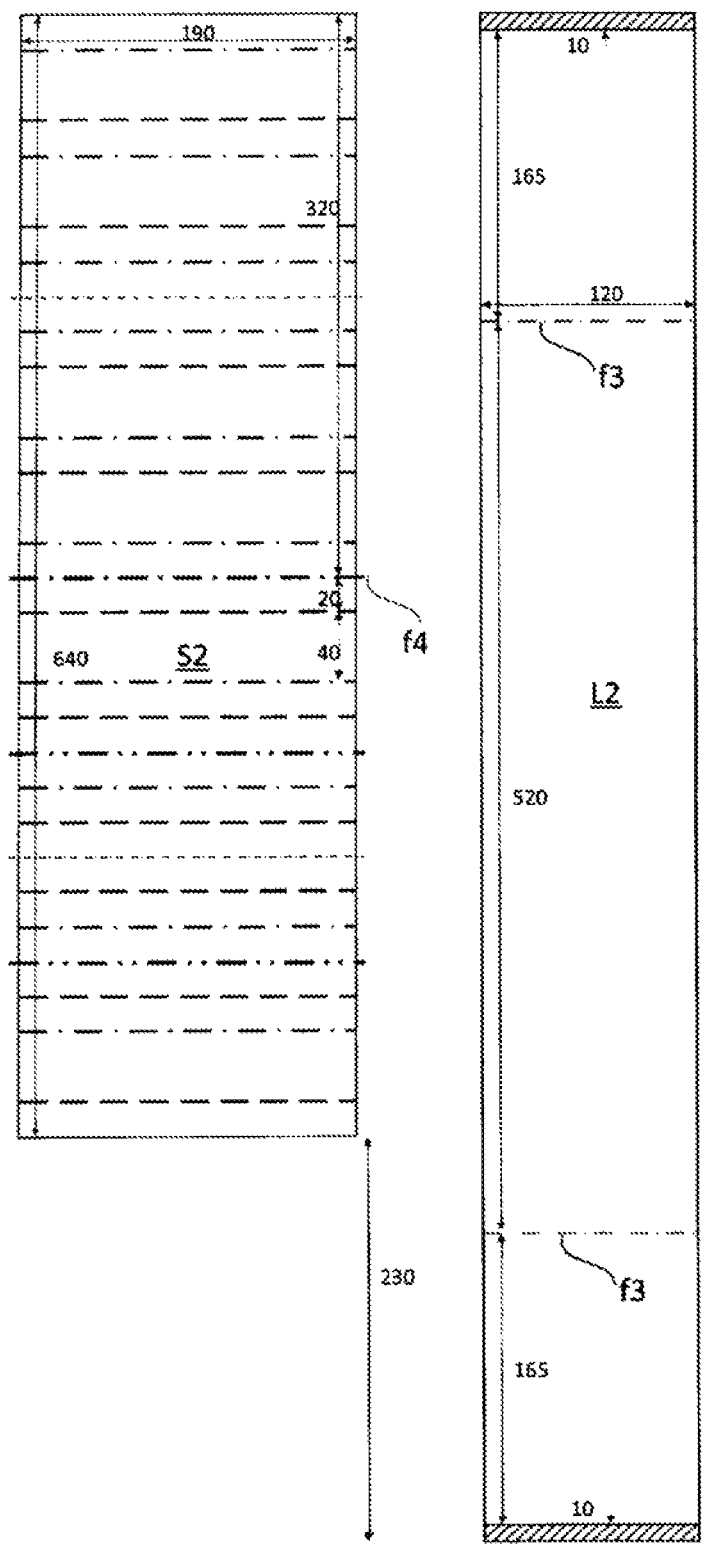
FIG. 7 is a plan view for illustrating a sheet made of paper to be used for manufacture of the feces collection sheet of the second example illustrated in FIG. 6.

FIG. 6(a) is a plan view for illustrating a second example of the feces collection sheet according to the present invention. FIG. 6(b) is a sectional view of a feces receiving portion illustrated in FIG. 6(a), which is taken along the line B-B in the front-and-rear direction. FIG. 7 is a plan view for illustrating a sheet made of paper to be used for manufacture of the feces collection sheet of the second example illustrated in FIG. 6.

For the feces collection sheet of the second example, the same configurations as those of the first example are denoted by the same reference symbols, and the description thereof is omitted. Thus, only configurations different from those of the first example are described.

Differences between the feces collection sheet S of the second example and the feces sapling sheet S of the first example reside in the configuration of the folded piece portion 10 of the feces receiving portion 2. The folded piece portion 10 of the second example is folded on the mountain creases 3 and the valley creases 4 which are provided in parallel to the right-and-left direction of the feces receiving portion 2, as illustrated in FIG. 6.

The end portions 3a of the mountain creases 3 and/or the end portions 4a of the valley creases 4 are fixed so as not to be unfoldable. In the second example, the end portions 3a of the mountain creases 3 and the end portions 4a of the valley creases 4 are fixed with the water-soluble tapes 5 each having a length of 12 cm.

In the second example, the width X1 between the front-side edge portion and the rear-side edge portion in a state in which the feces receiving portion 2 is folded is 12 cm, and the width Y1 in the right-and-left direction is 19 cm. The width X2 of a portion of the upper sheet 1 other than the feces receiving portion 2 is also 12 cm. The length Y2 of the upper sheet 1 in the right-and-left direction is 52 cm.

The lower sheet 9 having the same length and width as those of the upper sheet 1 is provided so as to extend from both of the right-side edge portion and the left-side edge portion of the upper sheet 1 to form the cylindrical shape, which is not visible under the upper sheet 1, and hence is not illustrated in FIG. 6(a).

For the mountain creases 3 and the valley creases 4 formed on the feces receiving portion 2 including the folded piece portion 10, as illustrated in FIG. 6(b), the mountain creases 3 are positioned on the front side and the valley creases 4 are positioned on the rear side with respect to the center 20 of the feces receiving portion 2.

The folded piece portion 10 configured as described above is pushed toward the lower sheet 9 to be unfolded from the center 20 of the feces receiving portion 2 in the front-and-rear direction. As a result, although not illustrated, the feces receiving portion 2 forms the three-dimensional shape that bulges toward the lower sheet 9.

The width X1 between the front-side edge portion and the rear-side edge portion of the feces receiving portion 2 formed into the three-dimensional shape falls within a range of from 12 cm to 15 cm, and the length Y1 in the right-and-left direction falls within a range of from 13 cm to 19 cm.

The remaining configuration is the same as that of the first example. Therefore, the description of the first example is used to omit the description of the remaining configuration of the second example.

Next, an example of a method of manufacturing the feces collection sheet S of the second example is described with reference to FIG. 7.

First, after two sheets, that is, sheets L2 and S2 made of paper are prepared as illustrated in FIG. 7, the feces collection sheet S is manufactured in the following steps. Numerical values in FIG. 7 represent lengths (mm).
(1) The sheet L2 is perforated along lines f3 which are located 175 mm away from both ends of the sheet L2 and is folded inwards.
(2) The sheet S2 is folded in half along a line f4.
(3) Four mountain creases (indicated by the alternate long and short dash lines) and six valley creases (indicated by the chain lines) are formed.
(4) The mountain creases are brought to folded edges toward the center so as to pleat the sheet S2.
(5) Both ends of the mountain creases and the valley creases of the sheet S2 are fixed to the sheet L2 with the water-soluble tapes. In this case, the water-soluble tapes are fixed to the sheet L2 so that the mountain creases and the valley creases on the sheet S2 are parallel to the right-and-left direction of the feces receiving portion.

The feces collection sheet S of the second example, which is configured as described above, is mounted to the toilet seat in the same manner as in the first example. Therefore, the description of the first example is used to omit the description regarding mounting of the feces collection sheet S.

Third Example

Figure 8:
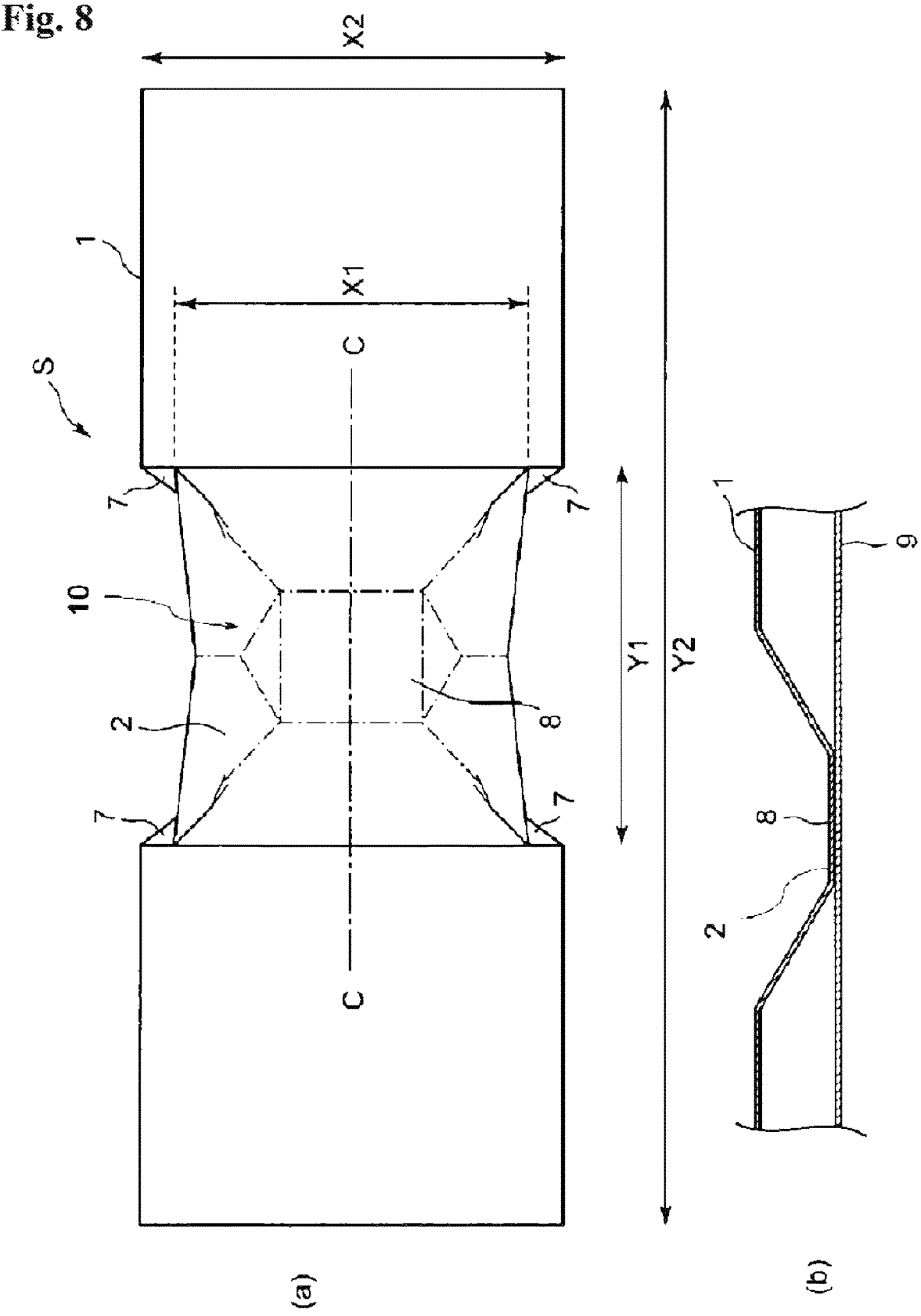
FIG. 8(a) is a plan view for illustrating a third example of the embodiment of the feces collection sheet according to the present invention.
FIG. 8(b) is a sectional view of the feces receiving portion illustrated in FIG. 8(a), which is taken along the line C-C in the right-and-left direction.
Figure 9:
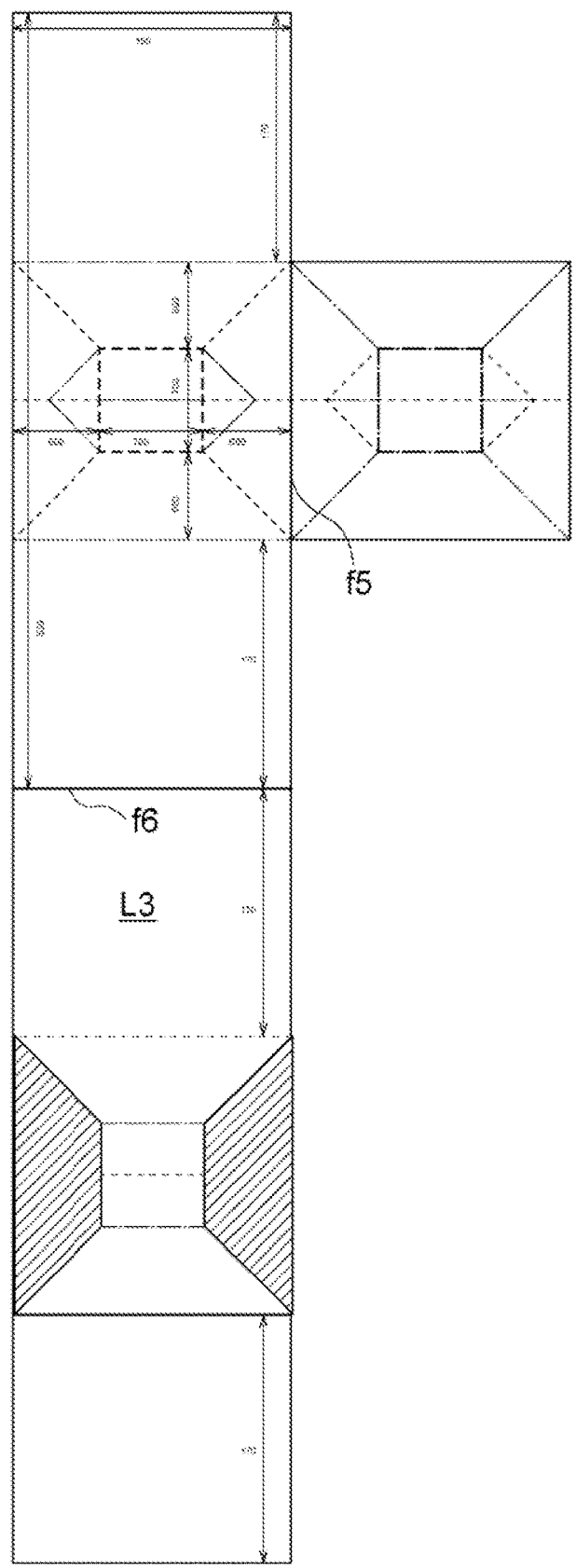
FIG. 9 is a plan view for illustrating a sheet made of paper to be used for manufacture of the feces collection sheet of the third example illustrated in FIG. 8.

FIG. 8(a) is a plan view for illustrating a third example of the feces collection sheet according to the present invention. FIG. 8(b) is a sectional view of the feces receiving portion illustrated in FIG. 8(a), which is taken along the line C-C in the right-and-left direction. FIG. 9 is a plan view for illustrating a sheet made of paper to be used for manufacture of the feces collection sheet of the third example illustrated in FIG. 8.

For the feces collection sheet of the third example, the same configurations as those of the first example are denoted by the same reference symbols, and the description thereof is herein omitted. Thus, only configurations different from those of the first example are described.

Differences between the feces collection sheet S of the third example and the feces collection sheet S of the first example reside in the configuration of the folded piece portion 10 of the feces receiving portion 2.

As illustrated in FIG. 8, the folded piece portion 10 of the third example is folded so that portions of the front-side edge portion and the rear-side edge portion of the upper sheet 1, which are located at four corners 7 of an upper end of the feces receiving portion 2, are valley-folded along inclination lines inclined in a direction toward the center of the feces receiving portion 2 and are fixed.

The width X1 between the front-side edge portion and the rear-side edge portion of the feces receiving portion 2 in a state in which the feces receiving portion 2 is unfolded to bulge toward the lower sheet 1 to form the three-dimensional shape falls within a range of from 16 cm to 17 cm, and the length Y1 in the right-and-left direction falls within a range of from 13 cm to 19 cm. The width X2 of the portion of the upper sheet 1 other than the feces receiving portion 2 in the front-and-rear direction is 19 cm. In the center of the feces receiving portion 2, a bottom portion 8 having a width of 7 cm and a length of 7 cm is formed.

The remaining configuration is the same as that of the first example. Therefore, the description of the first example is used to omit the description of the remaining configuration of the third example.

Next, an example of a method of manufacturing the feces collection sheet S of the third example is described with reference to FIG. 9.

First, after a sheet L3 made of paper is prepared as illustrated in FIG. 9, the feces collection sheet S is manufactured in the following steps. Numerical values in FIG. 9 represent lengths (mm).
(1) Hatched portions are cut away.
(2) The sheet L3 is folded on a line f5 and is fixed at two positions with a stapleless stapler.
(3) The sheet L3 is perforated along a line f6 and is folded.
(4) Ends of the sheet L3 are fixed at five positions with the stapleless stapler.
(5) The sheet L3 is creased on (two) diagonal lines in the center.
(6) The sheet L3 is creased along a square (four lines) in the center.
(7) The sheet L3 is creased so as to form the three-dimensional shape, and four corners thereof are fixed with the stapleless stapler.

The feces collection sheet S of the third example, which is configured as described above, is mounted to the toilet seat in the same manner as in the first example. Therefore, the description of the first example is used to omit the description regarding mounting of the feces collection sheet S.

Fourth Example

Figure 10:
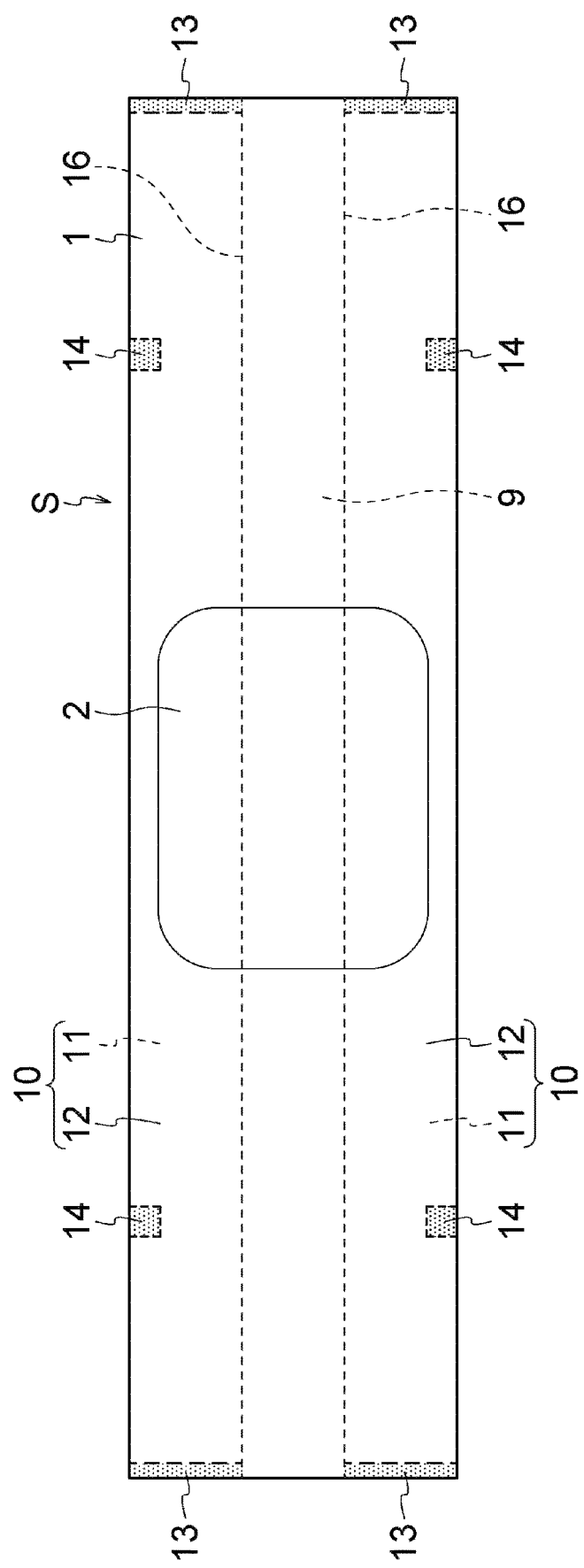
FIG. 10 is a plan view for illustrating a fourth example of the embodiment of the feces collection sheet according to the present invention.
Figure 11:
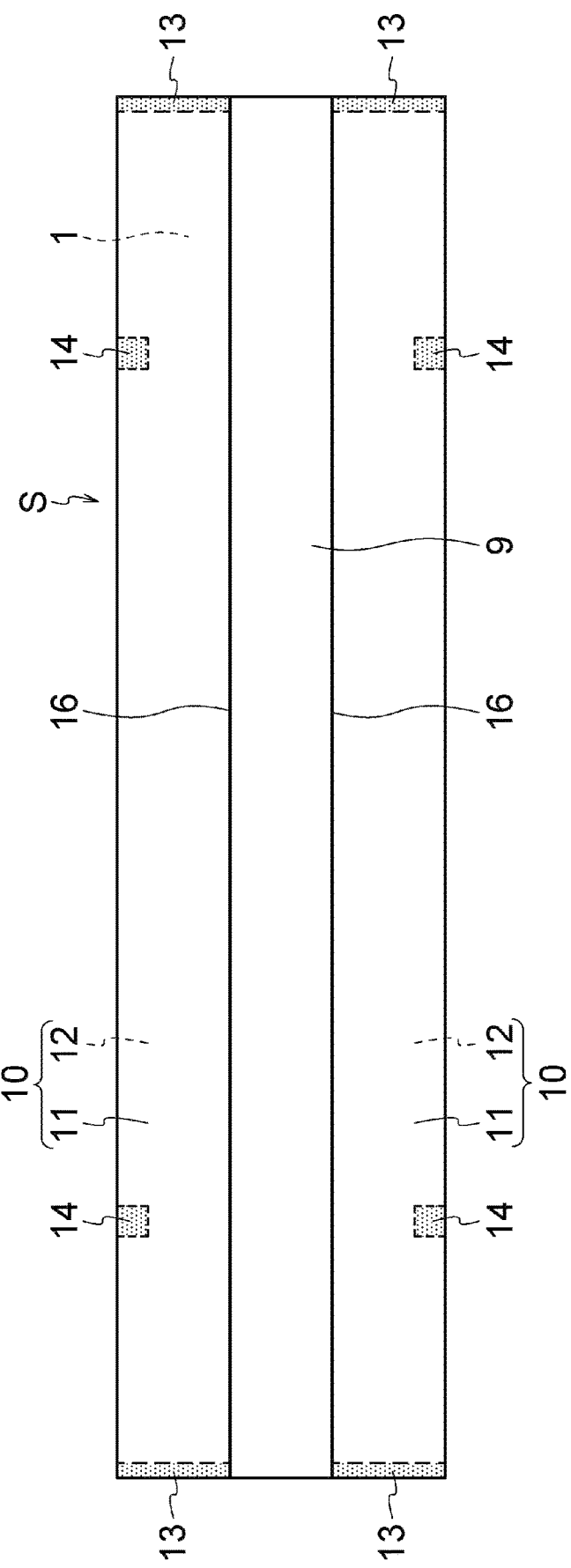
FIG. 11 is a bottom view of the feces collection sheet illustrated in FIG. 10.
Figure 12:
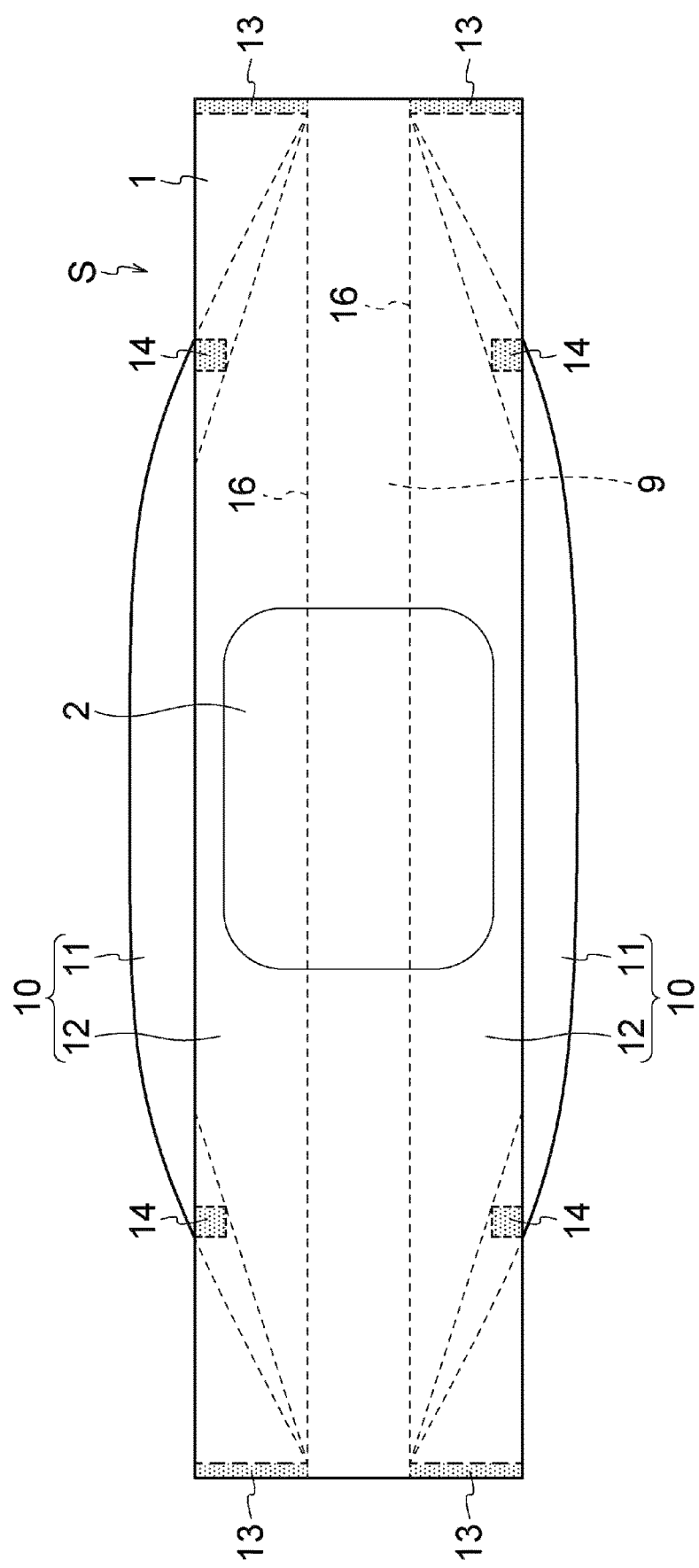
FIG. 12 is a plan view for illustrating a state in which the feces receiving portion of the feces collection sheet illustrated in FIG. 10 is unfolded to bulge toward the lower sheet to form the three-dimensional shape.
Figure 13:
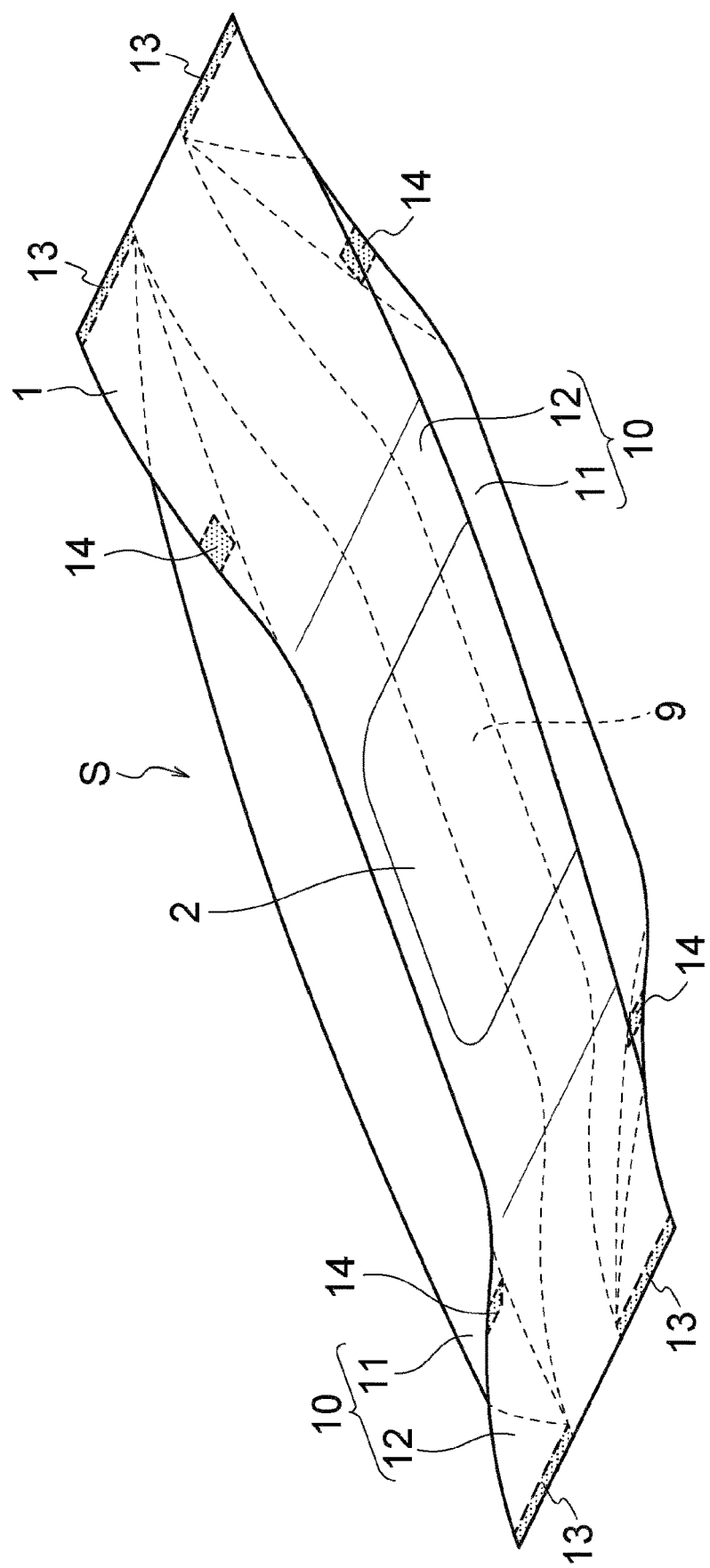
FIG. 13 is a perspective view of the feces collection sheet illustrated in FIG. 10.
Figure 14:
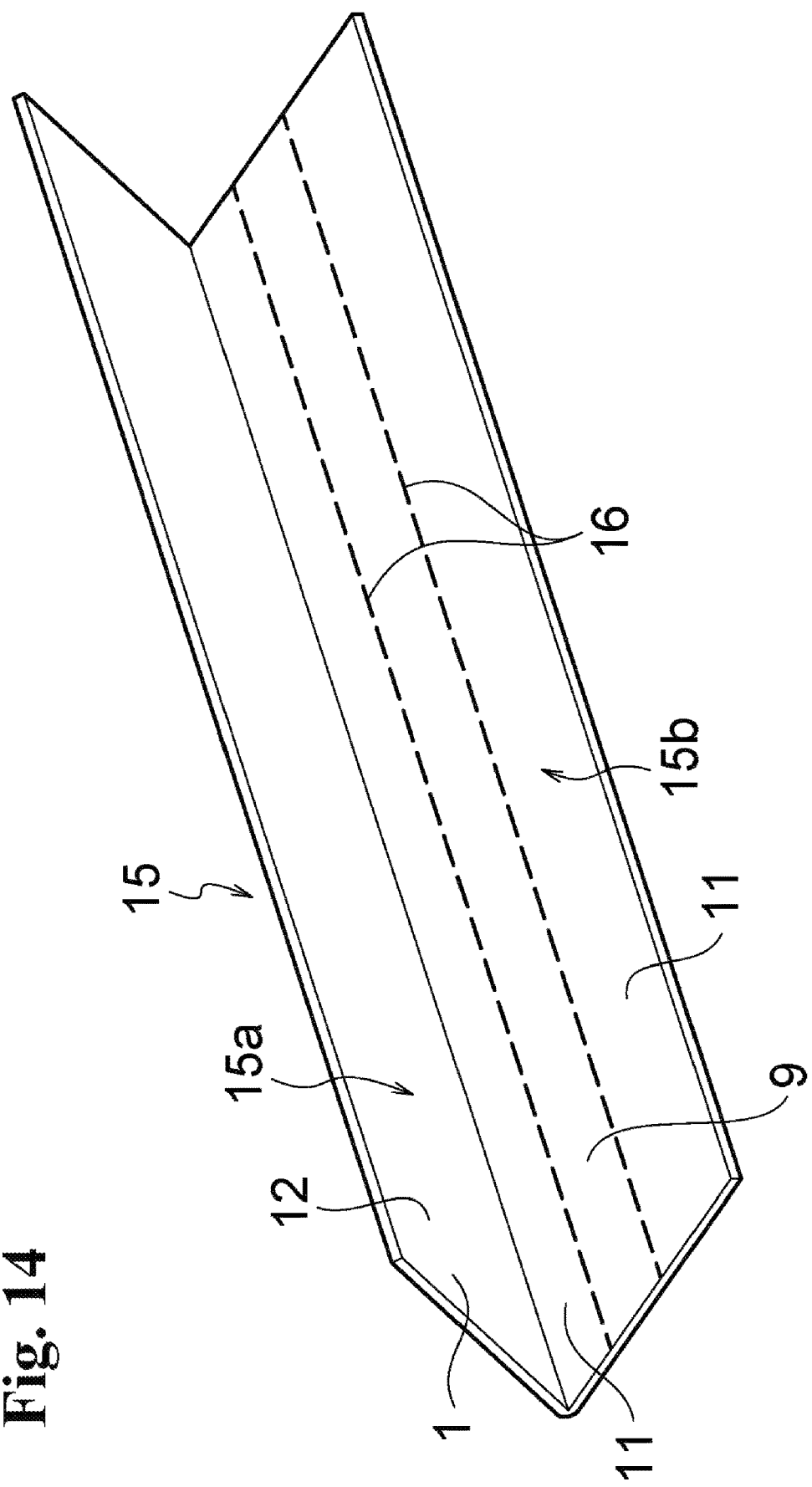
FIG. 14 is a process view for illustrating an example of a method of manufacturing the feces collection sheet of the fourth example illustrated in FIG. 10.
Figure 15:
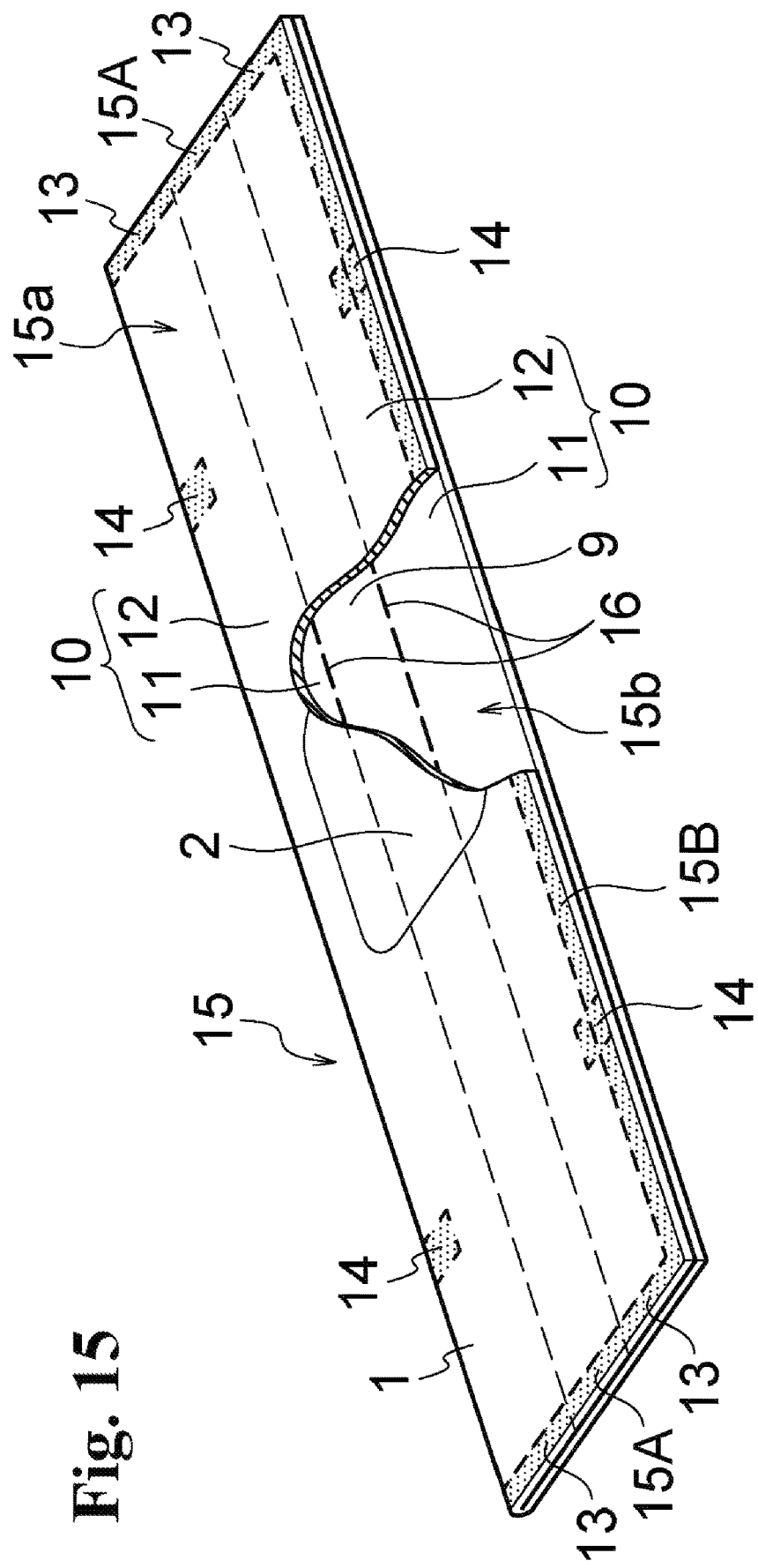
FIG. 15 is a process view for illustrating the example of the method of manufacturing the feces collection sheet of the fourth example illustrated in FIG. 10.
Figure 16:
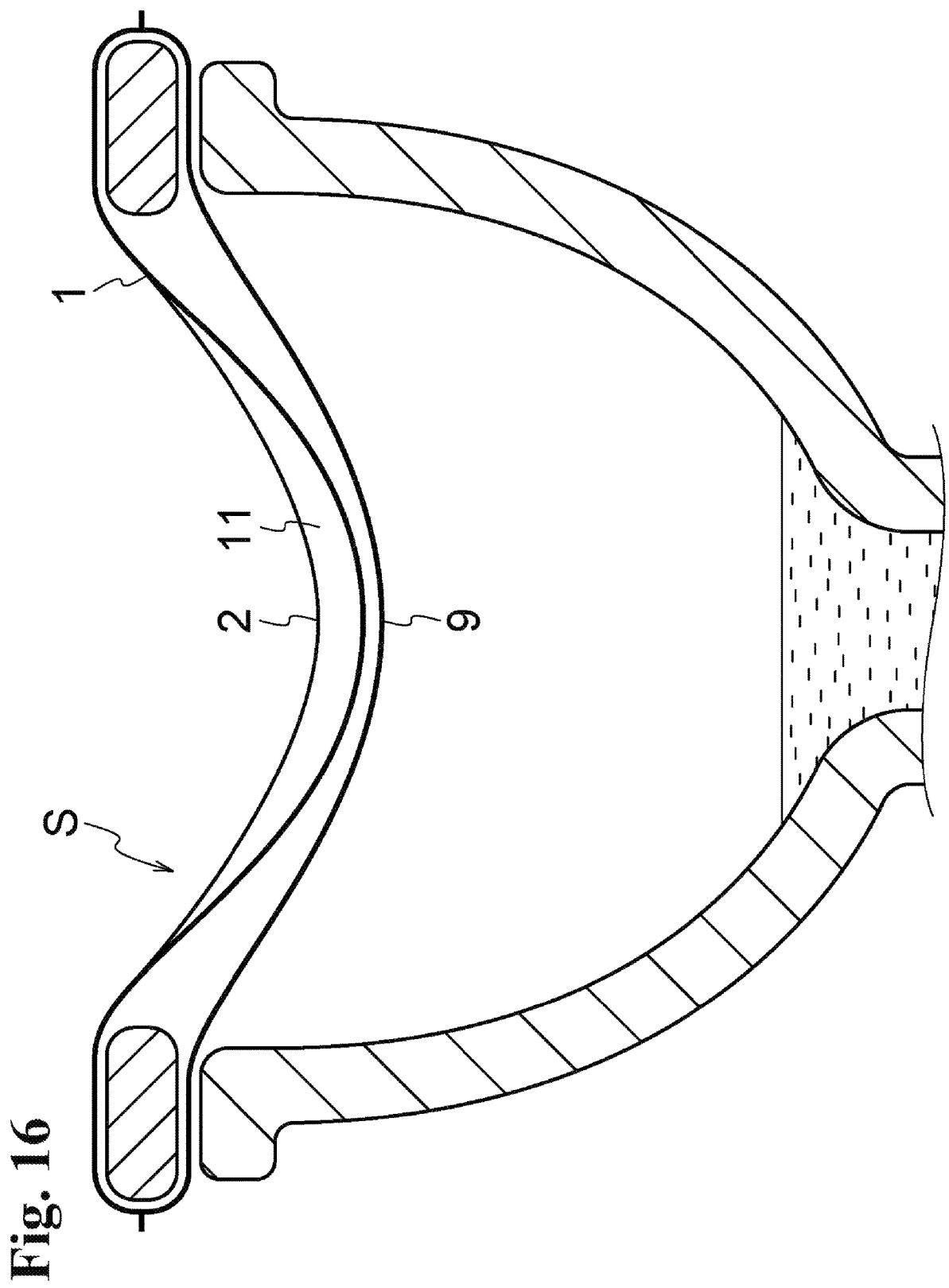
FIG. 16 is a front view for illustrating a state in which the feces collection sheet of the fourth example illustrated in FIG. 10 is placed on the toilet seat.

FIG. 10 is a plan view for illustrating a fourth example of the feces collection sheet according to the present invention. FIG. 11 is a bottom view of the feces collection sheet illustrated in FIG. 10. FIG. 12 is a plan view for illustrating a state in which the feces receiving portion of the feces collection sheet illustrated in FIG. 10 is unfolded to bulge toward the lower sheet to form the three-dimensional shape. FIG. 13 is a perspective view of the feces collection sheet illustrated in FIG. 12. FIG. 14 and FIG. 15 are process views for illustrating an example of a method of manufacturing the feces collection sheet of the fourth example. FIG. 16 is a front view for illustrating a state in which the feces collection sheet of the fourth example illustrated in FIG. 10 is placed on the toilet seat.

For the feces collection sheet of the fourth example, the same configurations as those of the first example are denoted by the same reference symbols, and the description thereof is herein omitted. Thus, only configurations different from those of the first example are described.

Differences between the feces collection sheet S of the fourth example and the feces sapling sheet S of the first example reside in the configuration of the folded piece portion 10 of the upper sheet 1.

In the fourth example, the folded piece portion 10 is formed by folding back the front-side edge portion and the rear-side edge portion of the upper sheet 1 to the back surface side and fixing a right end edge and a left end edge of each of back-side sheet piece portions 11, which are formed by being folded back, and a right end edge and a left end edge of a top-side sheet piece portion 12. The reference symbols 13 denote fixing portions at which the right and left end edges of each of the back-side sheet pieces 11 and the right and left end edges of the top-side sheet piece 12 are fixed to each other.

The folded piece portion 10 has fixing portions 14 each configured to fix the edge portion of the back-side sheet piece portion 11 and the edge portion of the top-side sheet piece portion 12 on the folded-back side at an approximately intermediate position between each of the right-side edge portion and the left-side edge portion of the upper sheet 1 and the feces receiving portion 2 formed in the center of the upper sheet 1.

The back-side sheet piece portions 11 of the folded piece portion 10, which are configured as described above, are brought to the top side of the top-side sheet piece portion 12 so as to be opened outward. In this manner, the feces receiving portion 2 is enabled to form the three-dimensional shape that bulges toward the lower sheet 9.

The folded piece portion 10 has the fixing portions 14 each configured to fix the edge portion of the back-side sheet piece portion 11 and the edge portion of the top-side sheet piece portion 12 on the folded-back side at the approximately intermediate position between each of the right-side edge portion and the left-side edge portion of the upper sheet 1 and the feces receiving portion 2 formed in the center of the upper sheet 1. Therefore, the fixing portions 14 prevent the back-side sheet portions 11 from being excessively opened outward so as to stabilize the bulging shape of the feces receiving portion 2.

The remaining configuration is the same as that of the first example. Therefore, the description of the first example is used to omit the description of the remaining configuration of the fourth example.

Next, an example of a method of manufacturing the feces collection sheet S of the fourth example is described with reference to FIG. 14 and FIG. 15.

First, a sheet base material 15 having a rectangular shape is folded in half. One sheet base material piece 15a is used as the top-side sheet piece portion 12 of the upper sheet 1.

Cutting lines 16 are formed in another sheet base material piece 15b with two perforated lines that are parallel to the horizontal line. Portions located on outer sides of the two cutting lines 16 are used as the back-side sheet piece portions 11 included in the folded piece portion 10 of the upper sheet 1, whereas a portion located on an inner side of the two cutting lines 16 is used as the lower sheet 9 (see FIG. 14).

Next, the two sheet base material pieces 15a and 15b are superposed on one another so that three open end edges of the two sheet base material pieces 15a and 15b are fixed to each other. The reference symbols 15A denote fixing portions at which the right and left open end edges of the sheet base material piece 15a and those of the sheet base material piece 15b are fixed to each other. The reference symbol 15B denotes a fixing portion at which an open front end edge of the sheet base material piece 15a and that of the sheet base material piece 15b are fixed to each other. The fixing portions 15A serve as the fixing portions 13 at which the right and left end edges of the back-side sheet pieces 11 and those of the top-side sheet piece 12 are fixed to each other. The fixing portion 15B forms a folded-back portion at which the top-side sheet piece portion 12 of the upper sheet 1 and the back-side sheet piece portions 11 are folded back to the back surface side of the top-side sheet piece portion 12. In this manner, the folded piece portion 10 is formed with the upper sheet 1.

Further, in the folded piece portion 10, the fixing portions 14 are formed by fixing the edge portion of the back-side sheet piece portion 11 and the edge portion of the top-side sheet piece portion 12 on the folded-back side at an approximately intermediate position between each of the right-side edge portion and the left-side edge portion of the upper sheet 1 and the feces receiving portion 2 formed in the center of the upper sheet 1 (see FIG. 15).

Although a fixing method used at the fixing portions 13, 14, 15A, and 15B is not particularly limited, there are exemplified a method using a water-soluble adhesive, a fixing method with a stapleless stapler, and a fixing method with heat or an ultrasonic wave.

The back-side sheet pieces 11 of the folded piece portion 10, which are configured as described above, are brought to the top side of the top-side sheet piece 12 so as to be opened outward. In this manner, the feces receiving portion 2 is enabled to form the three-dimensional shape that bulges toward the lower sheet 9 (see FIGS. 12 and 13).

The folded piece portion 10 has the fixing portions 14 each configured to fix the edge portion of the back-side sheet piece portion 11 and the edge portion of the top-side sheet piece portion 12 on the folded-back side at the approximately intermediate position between each of the right edge portion and the left edge portion of the upper sheet 1 and the feces receiving portion 2 formed in the center of the upper sheet 1. Therefore, the back-side sheet piece portions 11 are prevented from being excessively opened outward by the fixing portions 14. Thus, the feces receiving portion 2 can be unfolded to form the stable three-dimensional shape.

In order to mount the feces collection sheet S of the fourth example, which is configured as described above, to the toilet seat, similarly to the first example, the toilet seat is brought upright in the vertical direction or the toilet seat is lifted up from the toilet bowl by hand. After that, the toilet seat is inserted into the gap defined between the upper sheet 1 and the lower sheet 9 included in the feces collection sheet S. Then, after the feces collection sheet S is placed on the far side, the toilet seat is only required to be placed on the toilet bowl.

Subsequently, the position of the feces receiving portion 2 is adjusted so that the feces are easily received. Then, the back-side sheet pieces 11 of the folded piece portion 10 are brought to the top side of the top-side sheet piece 12 so as to be opened outward so that the feces receiving portion 2 is unfolded to form the three-dimensional shape that bulges toward the lower sheet 9 (see FIG. 16).

The remaining configuration is the same as that of the first example. Therefore, the description of the first example is used to omit the description of the remaining configuration of the fourth example.

REFERENCE SIGNS LIST

S feces collection sheet
1 upper sheet 2 feces receiving portion
3 mountain crease
3a end portion of mountain crease
4 valley crease
4a end portion of valley crease
5 water-soluble tape
6 cutting portion
7 corner of upper end of feces receiving portion
8 bottom portion
9 lower sheet
10 folded piece portion
10a folded piece
11 back-side sheet piece portion
12 top-side sheet piece portion
13, 14 fixing portion
15 sheet base material
15a, 15b sheet base material piece
15A, 15B fixing portion
16 cutting line
20 center of feces receiving portion
X1 width between front-side edge portion and rear-side edge portion
X2 width of portion of upper sheet other than feces receiving portion
Y1 length in right-and-left direction at feces receiving portion
Y2 length of upper sheet in right-and-left direction

The invention claimed is:

1. A feces collection sheet, which has a cylindrical shape, comprising:
an upper sheet having a feces receiving portion in a center of the upper sheet; and
a lower sheet, which is provided so as to extend from both of a right-side edge portion and a left-side edge portion of the upper sheet and is configured to define a gap with the upper sheet to allow insertion of a toilet seat therethrough,
wherein the upper sheet and the lower sheet are made of a material having a water-soluble material property,
wherein the upper sheet has a folded piece portion to be unfolded to enable the feces receiving portion to form a three-dimensional shape that bulges toward the lower sheet,
wherein the folded piece portion of the upper sheet is formed by folding back a front-side edge portion and a rear-side edge portion of the upper sheet to a back surface side of the upper sheet, and fixing a right end edge and a left end edge of each of back-side sheet piece portions, which are formed by being folded back, to a right end edge and a left end edge of a top-side sheet piece portion, respectively,
wherein the feces receiving portion is enabled to form the three-dimensional shape that bulges toward the lower sheet by bringing the back-side sheet piece portions to the top side of the top-side sheet piece portion so as to open the back-side sheet piece portions outward,
wherein the upper sheet and the lower sheet are formed of two sheet base material pieces obtained by folding a sheet base material having a rectangular shape in half,
wherein one of the sheet base material pieces is used as the top-side sheet piece portion of the upper sheet, whereas two cutting lines being parallel to a right-and-left direction of the feces collection sheet are formed in another of the sheet base material pieces,
wherein portions located on outer sides of the two cutting lines are used as the back-side sheet piece portions that form the folded piece portion of the upper sheet, whereas a portion located on an inner side of the two cutting lines is used as the lower sheet, and
wherein, after the two sheet base material pieces obtained by folding the sheet base material in half are superposed on one another, three open end edges of the two sheet base material pieces having been superposed on one another are fixed to each other.

2. A feces collection sheet, which has a cylindrical shape, comprising:
an upper sheet having a feces receiving portion in a center of the upper sheet; and
a lower sheet, which is provided so as to extend from both of a right-side edge portion and a left-side edge portion of the upper sheet and is configured to define a gap with the upper sheet to allow insertion of a toilet seat therethrough,
wherein the upper sheet and the lower sheet are made of a material having a water-soluble material property,
wherein the upper sheet has a folded piece portion to be unfolded to enable the feces receiving portion to form a three-dimensional shape that bulges toward the lower sheet,
wherein the upper sheet and the lower sheet, which are made of the material having the water-soluble material property, are made of water-soluble paper,
wherein the folded piece portion of the upper sheet is formed by folding back a front-side edge portion and a rear-side edge portion of the upper sheet to a back surface side of the upper sheet, and fixing a right end edge and a left end edge of each of back-side sheet piece portions, which are formed by being folded back, to a right end edge and a left end edge of a top-side sheet piece portion, respectively,
wherein the feces receiving portion is enabled to form the three-dimensional shape that bulges toward the lower sheet by bringing the back-side sheet piece portions to the top side of the top-side sheet piece portion so as to open the back-side sheet piece portions outward,
wherein the upper sheet and the lower sheet are formed of two sheet base material pieces obtained by folding a sheet base material having a rectangular shape in half,
wherein one of the sheet base material pieces is used as the top-side sheet piece portion of the upper sheet, whereas two cutting lines being parallel to a right-and-left direction of the feces collection sheet are formed in another of the sheet base material pieces,
wherein portions located on outer sides of the two cutting lines are used as the back-side sheet piece portions that form the folded piece portion of the upper sheet, whereas a portion located on an inner side of the two cutting lines is used as the lower sheet, and
wherein, after the two sheet base material pieces obtained by folding the sheet base material in half are superposed on one another, three open end edges of the two sheet base material pieces having been superposed on one another are fixed to each other.

\* \* \* \* \*